(12) United States Patent
Trudeau

(10) Patent No.: US 7,976,550 B2
(45) Date of Patent: Jul. 12, 2011

(54) INSERTION INSTRUMENT FOR ARTIFICIAL DISCS

(75) Inventor: Jeffrey L. Trudeau, Marquette, MI (US)

(73) Assignee: Pioneer Surgical Technology, Marquette, MI (US)

( * ) Notice: Subject to any disclaimer, the term of this patent is extended or adjusted under 35 U.S.C. 154(b) by 956 days.

(21) Appl. No.: 11/836,234

(22) Filed: Aug. 9, 2007

(65) Prior Publication Data

US 2008/0039860 A1     Feb. 14, 2008

Related U.S. Application Data

(60) Provisional application No. 60/822,027, filed on Aug. 10, 2006, provisional application No. 60/846,859, filed on Sep. 22, 2006, provisional application No. 60/909,285, filed on Mar. 30, 2007.

(51) Int. Cl.
*A61B 17/58* (2006.01)
*A61B 17/60* (2006.01)
*A61F 2/00* (2006.01)

(52) U.S. Cl. ...................................................... 606/99

(58) Field of Classification Search ................ 606/99, 606/86 A, 914
See application file for complete search history.

(56) References Cited

U.S. PATENT DOCUMENTS

| | | |
|---|---|---|
| 4,374,523 A | 2/1983 | Yoon |
| 4,566,466 A | 1/1986 | Ripple et al. |
| 4,899,761 A | 2/1990 | Brown et al. |
| 5,084,057 A * | 1/1992 | Green et al. ............... 606/142 |
| 5,542,949 A | 8/1996 | Yoon |
| 5,562,736 A | 10/1996 | Ray et al. |
| 6,478,801 B1 | 11/2002 | Ralph et al. |
| 6,607,559 B2 | 8/2003 | Ralph et al. |
| 6,652,533 B2 | 11/2003 | O'Neil |
| 6,669,730 B2 | 12/2003 | Ralph et al. |
| 6,673,113 B2 | 1/2004 | Ralph et al. |

(Continued)

FOREIGN PATENT DOCUMENTS
WO          199100713          1/1991

OTHER PUBLICATIONS

International Search Report dated Jul. 3, 2008, from the International Searching Authority in corresponding International (PCT) Application No. PCT/US2007/075693.

*Primary Examiner* — Eduardo C Robert
*Assistant Examiner* — Sameh Boles
(74) *Attorney, Agent, or Firm* — Fitch, Even, Tabin & Flannery

(57) ABSTRACT

An insertion instrument for inserting an implant in an intervertebral space is provided. The instrument includes an elongate shaft having proximate and distal ends with a longitudinal axis therebetween. On the distal end of the elongate shaft is a gripping device capable of shifting from a holding configuration for securing a portion of the implant relative the distal end and a releasing configuration to permit removal of the implant portion from the elongate shaft. The instrument includes a handle configured to be held with a generally neutral wrist position to permit comfortable use of the instrument. The instrument also includes an actuating mechanism coupled between the gripping device and the handle that is operable to configure the gripping device in the holding configuration upon an initial actuation thereof and the releasing configuration upon a subsequent actuation thereof.

26 Claims, 18 Drawing Sheets

U.S. PATENT DOCUMENTS

| | | |
|---|---|---|
| 6,824,565 B2 | 11/2004 | Muhanna et al. |
| 6,863,689 B2 | 3/2005 | Ralph et al. |
| 6,984,246 B2 | 1/2006 | Huang |
| 2002/0065560 A1 | 5/2002 | Varga et al. |
| 2002/0111683 A1 | 8/2002 | Ralph et al. |
| 2002/0111687 A1 | 8/2002 | Ralph et al. |
| 2002/0151979 A1 | 10/2002 | Lambrecht et al. |
| 2003/0009227 A1 | 1/2003 | Lambrecht et al. |
| 2003/0014113 A1 | 1/2003 | Ralph et al. |
| 2003/0014115 A1 | 1/2003 | Ralph et al. |
| 2003/0040802 A1 | 2/2003 | Errico et al. |
| 2003/0069586 A1 | 4/2003 | Errico et al. |
| 2003/0069642 A1 | 4/2003 | Ralph et al. |
| 2003/0069643 A1 | 4/2003 | Ralph et al. |
| 2003/0078590 A1 | 4/2003 | Errico et al. |
| 2003/0078662 A1 | 4/2003 | Ralph et al. |
| 2003/0093155 A1 | 5/2003 | Lambrecht et al. |
| 2003/0130667 A1 | 7/2003 | Lin |
| 2003/0149438 A1 | 8/2003 | Nichols et al. |
| 2003/0204362 A1 | 10/2003 | Beresford et al. |
| 2003/0216810 A1 | 11/2003 | Ralph et al. |
| 2003/0229358 A1 | 12/2003 | Errico et al. |
| 2004/0010316 A1 | 1/2004 | William et al. |
| 2004/0024462 A1 | 2/2004 | Ferree et al. |
| 2004/0030390 A1 | 2/2004 | Ferree |
| 2004/0030391 A1 | 2/2004 | Ferree |
| 2004/0034426 A1 | 2/2004 | Errico et al. |
| 2004/0049280 A1 | 3/2004 | Cauthen |
| 2004/0068321 A1 | 4/2004 | Ferree |
| 2004/0093088 A1 | 5/2004 | Ralph et al. |
| 2004/0098129 A1 | 5/2004 | Lin |
| 2004/0133132 A1 | 7/2004 | Chappuis |
| 2004/0133278 A1 | 7/2004 | Marino et al. |
| 2004/0133280 A1 | 7/2004 | Trieu |
| 2004/0143331 A1 | 7/2004 | Errico et al. |
| 2004/0143332 A1 | 7/2004 | Krueger et al. |
| 2004/0148027 A1 | 7/2004 | Ferree et al. |
| 2004/0148028 A1 | 7/2004 | Ferree et al. |
| 2004/0153065 A1 | 8/2004 | Lim |
| 2004/0153158 A1 | 8/2004 | Errico et al. |
| 2004/0153159 A1 | 8/2004 | Cauthen |
| 2004/0167534 A1 | 8/2004 | Errico et al. |
| 2004/0167626 A1 | 8/2004 | Geremakis et al. |
| 2004/0167628 A1 | 8/2004 | Foley |
| 2004/0176843 A1 | 9/2004 | Zubok et al. |
| 2004/0176845 A1 | 9/2004 | Zubok et al. |
| 2004/0176848 A1 | 9/2004 | Zubok et al. |
| 2004/0186577 A1 | 9/2004 | Ferree |
| 2004/0225295 A1 | 11/2004 | Zubok et al. |
| 2005/0027360 A1 | 2/2005 | Webb et al. |
| 2005/0033305 A1 | 2/2005 | Schultz |
| 2005/0033437 A1 | 2/2005 | Bao et al. |
| 2005/0033438 A1 | 2/2005 | Schultz et al. |
| 2005/0038445 A1 | 2/2005 | Errisco et al. |
| 2005/0038515 A1 | 2/2005 | Kunzler |
| 2005/0038516 A1 | 2/2005 | Spoonamore |
| 2005/0055097 A1 | 3/2005 | Grunberg et al. |
| 2005/0060035 A1 | 3/2005 | Errico et al. |
| 2005/0071012 A1 | 3/2005 | Serhan et al. |
| 2005/0085917 A1 | 4/2005 | Marnay et al. |
| 2005/0096745 A1 | 5/2005 | Andre et al. |
| 2005/0113842 A1 | 5/2005 | Bertagnoli et al. |
| 2005/0119752 A1 | 6/2005 | Williams et al. |
| 2005/0131541 A1 | 6/2005 | Trieu |
| 2005/0143820 A1 | 6/2005 | Zucherman et al. |
| 2005/0143824 A1 | 6/2005 | Richelsoph et al. |
| 2005/0154463 A1 | 7/2005 | Trieu |
| 2005/0154464 A1 | 7/2005 | Humphreys et al. |
| 2005/0154466 A1 | 7/2005 | Humphreys et al. |
| 2005/0154468 A1 | 7/2005 | Rivin |
| 2005/0192670 A1 | 9/2005 | Zubok et al. |
| 2005/0192671 A1* | 9/2005 | Bao et al. .................. 623/17.14 |
| 2005/0203538 A1 | 9/2005 | Lo et al. |

* cited by examiner

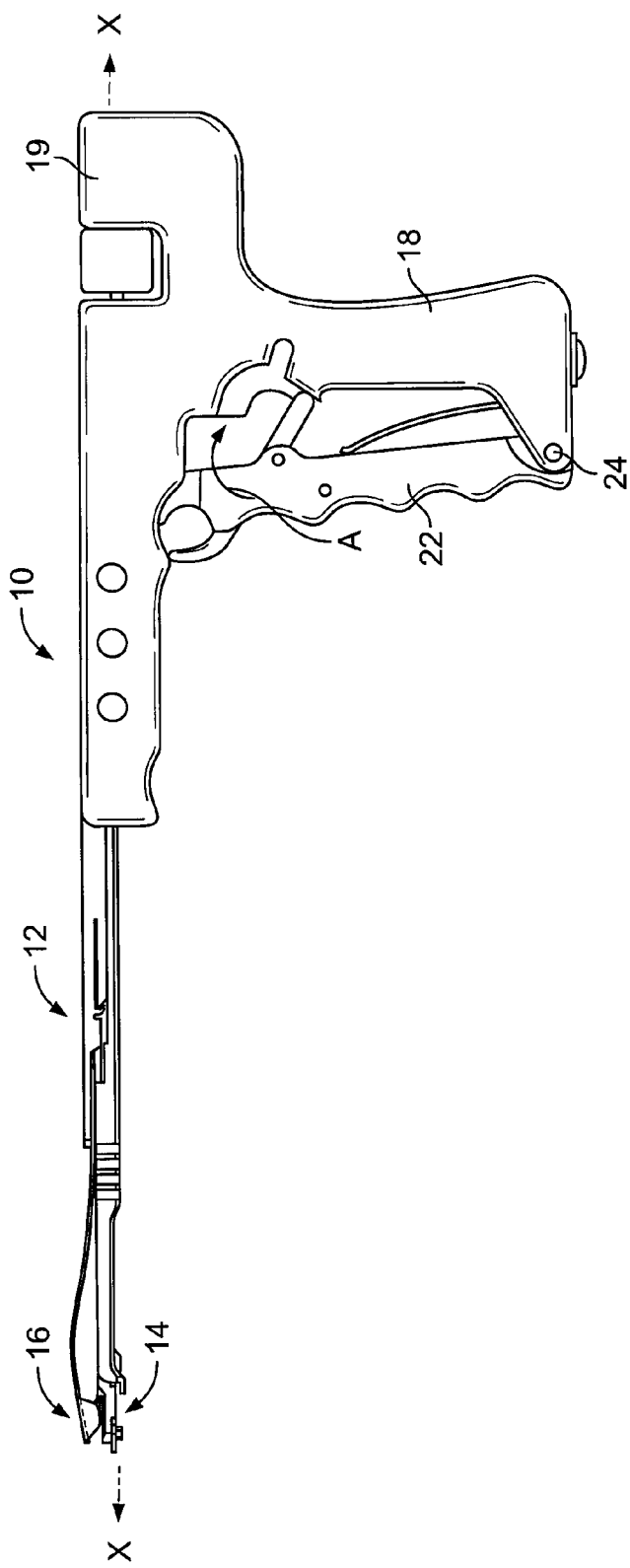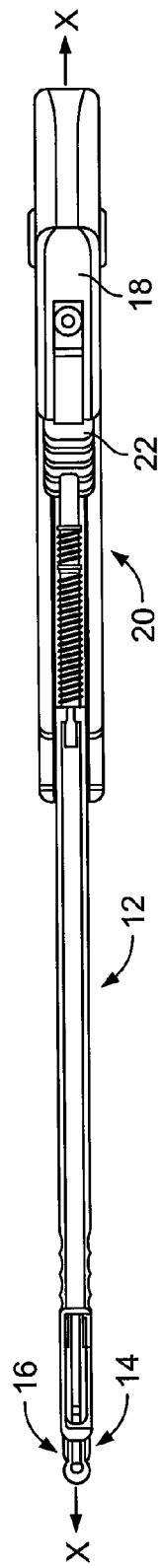
FIG. 4
FIG. 5

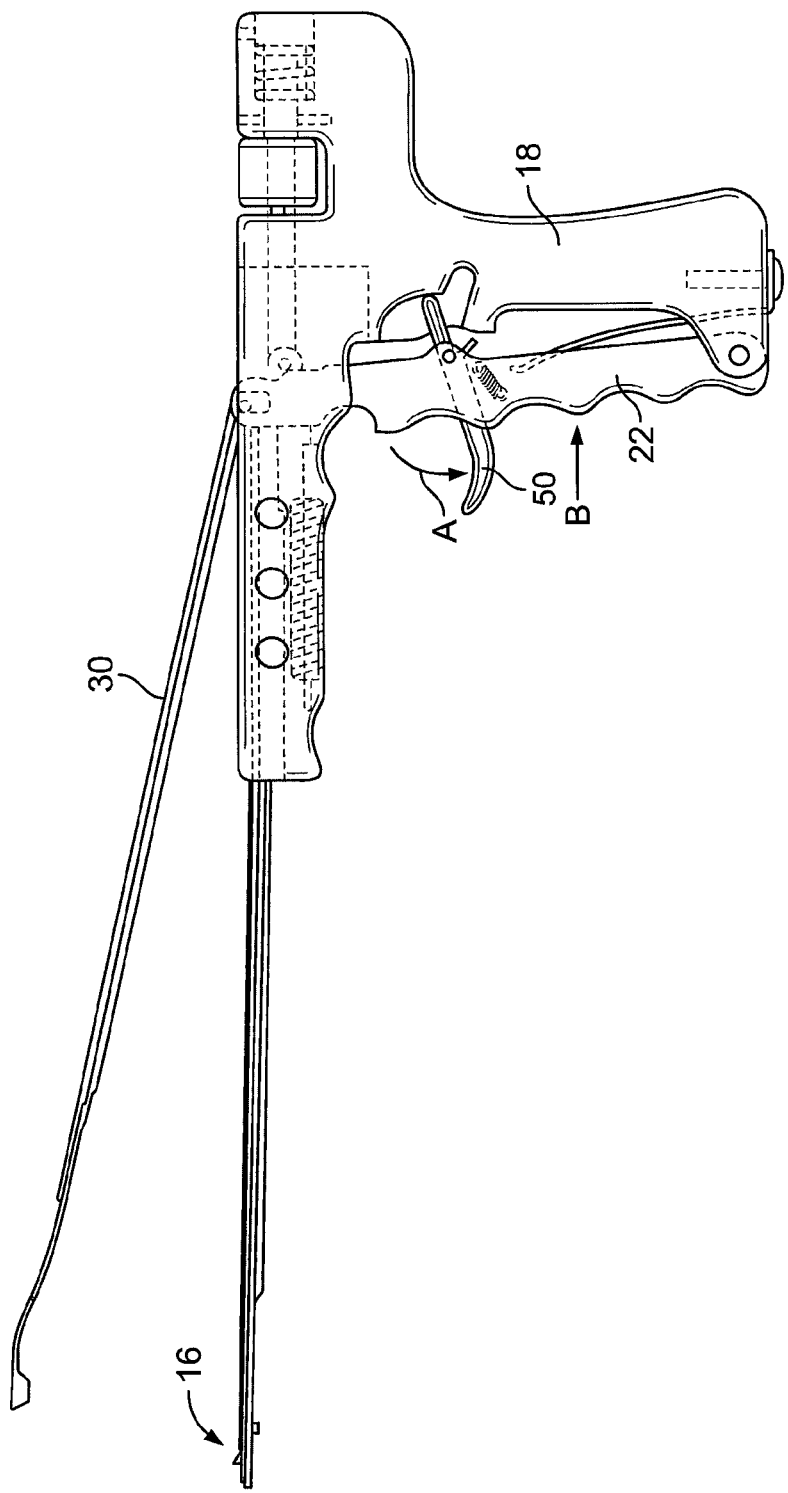
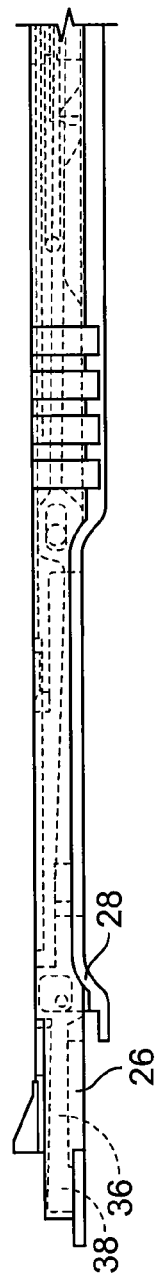
FIG. 15
FIG. 16

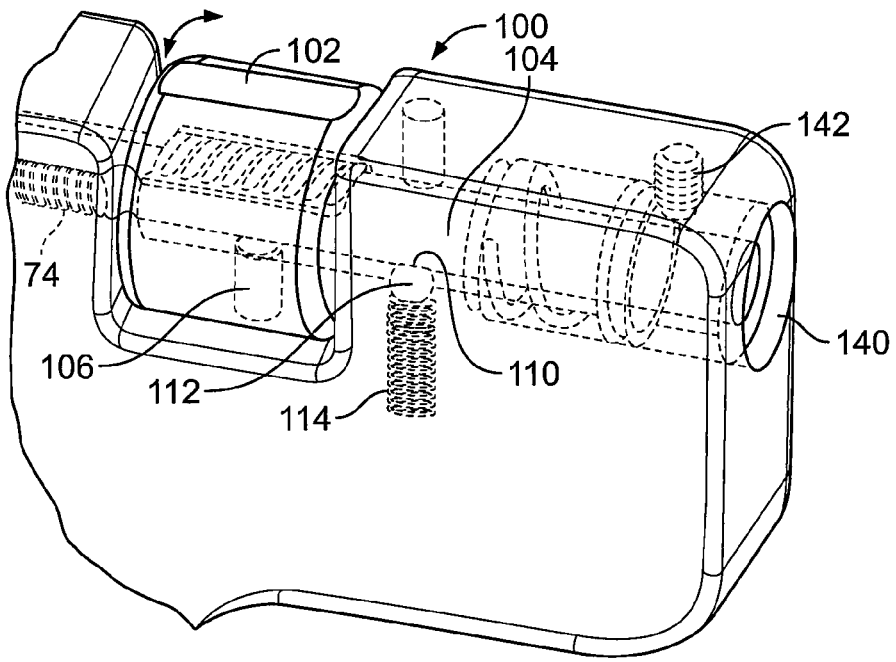
FIG. 27
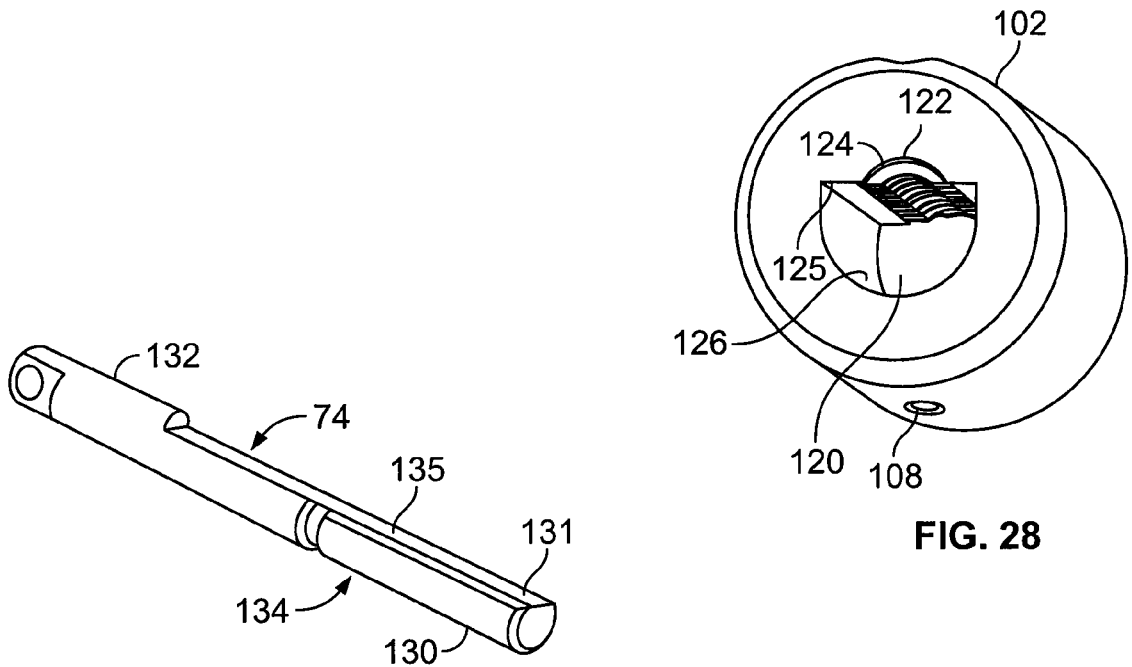
FIG. 28
FIG. 29

INSERTION INSTRUMENT FOR ARTIFICIAL DISCS

CROSS-REFERENCE TO RELATED APPLICATIONS

This application claims benefit of U.S. Provisional Application No. 60/822,027, filed Aug. 10, 2006, U.S. Provisional Application No. 60/846,859, filed Sep. 22, 2006 and U.S. Provisional Application No. 60/909,285, filed Mar. 30, 2007, all of which are hereby incorporated by reference as if reproduced herein in their entirety.

FIELD

This invention relates to insertion instruments for artificial disc devices and other implants used in the vertebrae, and in particular, insertion instruments used to hold multiple piece implants for insertion into the vertebrae.

BACKGROUND

The most common orthopedic condition for which professional medical treatment is sought is lower back pain. Although many factors may be responsible for causing lower back pain, a principal factor is damage or degeneration of an intervertebral spinal disc resulting in impingement on the nerve system, specifically the spinal cord, located within the spine. Such impingement may result in, for instance, loss of mobility, urinary and fecal incontinence, and sciatica or pain experienced in the extremities.

Damage to or degeneration of a spinal disc can result from a number of factors such as abuse or age. The disc itself is composed primarily of an annulus and a nucleus contained therein. The annulus is a fibrous annular piece that attaches to the adjacent vertebrae and contains the nucleus, which is in turn a gel like viscous material capable of shock absorption and flowable to permit poly axial rotation and resilient compression of the vertebrae and spine. Most frequently, disc degeneration results from damage occurring to the annulus such that the flowable nucleus material may leak or seep out of the annulus. Disc degeneration also can occur in other ways, such as by being deprived of nutrient flow leading to a dried disc susceptible to damage. Because the nuclear material is flowable, extensive damage to the annulus is not necessary for leakage to occur.

Currently, approaches to treatment of spinal problems directly affecting the spinal cord are numerous. For instance, immobilization and high doses of corticosteroids may be employed. The dominant surgical procedures for treatment of these problems are spinal fusion and discectomy. Fusion is a method where adjacent vertebrae are immobilized so that they permanently secure to each other by having bone growth between and to the vertebrae, while discectomy involves removal of a portion or an entirety of a spinal disc.

However, the current practice of each of these procedures typically has certain limitations. With fusion, making a portion of the spine generally rigid produces a reduction in mobility, and drastically alters normal load distribution along the spinal column. Due to these factors, the non fused portions of the spine experience stress and strain that are significantly increased over normal physiological motions. The increased stress and strain on the non fused portions may lead to accelerated disc degeneration of the non fused portions, particularly the adjacent levels of the spine.

Discectomy is effective for relieving sciatic pain by removing the damaged or herniated disc tissue compressing the spinal nerves. However, current discectomy often may lead to a reduction of the disc space between adjacent vertebrae, as well as instability in the affected portion of the spine. Such long term effects with current discectomy often result in further surgery several years after the initial discectomy surgery.

A recent, though not new, development for spinal surgery of this type is a procedure known as disc arthroplasty for restoring or reconstructing the disc using a prosthesis to replace a portion or entirety of the damaged disc. The primary objective of disc arthroplasty is to restore or maintain the normal disc anatomy and functions, while addressing and treating the causes of the pain. However, little success has been experienced with prosthetic disc implants due to the complexity of the natural disc structure and biomechanical properties of a natural spinal disc. As used herein, the term natural refers to normal tissue including portions of the spine and the disc.

Two types of prostheses for disc arthroplasty are currently believed to merit further development by medical science and research. One type is a total disc prosthesis, or TDP, where the entire spinal disc is replaced after radical discectomy. A typical TDP includes structures that together attempt to mimic the properties of a natural disc.

The other type is a disc nucleus prosthesis, or DNP, that is used to replace only the nucleus of a spinal disc after a nucleotomy while retaining the annulus of the disc and, possibly, the end plates intact. As discussed above, failure of the natural disc does not require extensive damage to the annulus, and the annulus would often be capable of retaining a non flowing prosthetic nucleus. Implantation of a DNP involves clearing of the natural nucleus from the annulus through the procedure known as nucleotomy, and inserting the DNP within the annulus. Accordingly, DNPs are typically smaller and require less extensive surgery than TDPs while still mimicking some of the biomechanical properties of a natural intervertebral disc. Herein, the term artificial disc, device, or implant can refer to either a TDP or a DNP.

In using disc implants, one problem relates to the preparation for the surgical procedure for implanting either the TDPs or DNPs. The time required for preparing for surgery, and specifically preparing the implants and inserters for use, can be important for both patient welfare and in terms of cost efficiency. For instance, if only one of the ends of the implant is configured for gripping by an inserter tool, this requires the medical personnel to locate the proper end of the implant and then connect it to the inserter. Extra time is wasted when an implant has otherwise similarly configured ends such that it is difficult to easily determine which end of the implant attaches to the inserter. The problem is compounded when the implant has multiple components (such as a top and bottom portion), and the medical personnel need to first properly match the disc components to each other so that the ends of each component configured to connect to each other are properly aligned with each other before attachment of the disc to the inserter. This can waste time during preparation for the surgical procedure. Accordingly, an artificial disc would be desirable that has portions that do not only connect with each other in one configuration and require that the disc be mounted on an inserter tool in a single orientation.

Other improvements specifically for the DNP procedure would be desirable. As mentioned above, a DNP requires less extensive surgery than for a TDP since it replaces only part of the disc. Implantation of most known DNPs with pre formed dimensions generally requires a 5 to 6 mm, or larger, incision in the annulus for implantation. The incision, however, should be kept as small as possible to hold the DNP within the annulus without using anchors on the DNP that extend into the end plates of the vertebrae for securing the DNP. The minimal invasiveness of the procedure results in minimal recovery and post surgical pain, and interbody fusion remains a viable revision surgery. Thus, maintaining a small incision and keeping damage to the annulus to a minimum is a high priority. Therefore, it would be desirable to provide a DNP and inserter that does not require an enlarged incision and does not significantly damage the annulus or other tissue during insertion and placement of the DNP.

Another problem with DNP structure and the surgical procedures involving DNP relate to the positioning of the artificial disc within the nuclear space. For some DNPs, once the implant is positioned in the nuclear space, it must be rotated in order to position it properly for providing its full range of motion and its full shock absorption capabilities to the patient. Thus, a DNP and an inserter that manipulates the DNP within the nuclear space without causing damage to the annulus are also desired.

Current insertion instruments for artificial disc devices further complicate the surgical procedures due to the requirement that the surgeon manipulate multiple controls to grasp, hold, and release the implant as well as require the surgeon to hold such instruments using a generally un-natural wrist position. One such example is the insertion tool described in U.S. Pat. No. 6,478,801 to Ralph et al. The tool of the '801 patent is a generally elongate member having a handle on one end thereof aligned with a longitudinal axis of the handle. On a lower portion of the handle is a first control to mechanically hold the implant to a compression assembly on an opposite end of the elongate member. On an upper portion of the handle is a second, separate control to release the implant. In use, with the handle aligned along the longitudinal axis of the instrument, the surgeon is required to hold the instrument with some degree of wrist flexion, extension, ulnar deviation, or radial deviation in order to insert a connected implant into the vertebral space of a patient. This un-natural positioning of the surgeon's wrist can render the delicate insertion procedure of the implant more difficult. Moreover, while grasping the instrument with such wrist positioning, the surgeon is also required to manipulate multiple controls to both hold and release the implant, which further complicates the operation of the instrument.

Other instruments, such as those described in US Patent Publication Nos. 2003/0149438A1 to Nichols et al. and 2005/0060035A1 to Errico et al. also employ instruments having handles aligned with the longitudinal axis of the tool shafts, and therefore, may also require some degree of un-natural wrist positioning during use. These instruments, however, also have controls that require both hands of the surgeon to operate the instrument. That is, one hand of the surgeon holds the instrument while the other hand operates a control to grasp and release the implant on the opposite end of the shaft. Such instruments complicate insertion of an implant because the surgeon must use both handles to manipulate the instrument.

Accordingly, there is a desire for an insertion instrument to hold an artificial disc device for insertion into a vertebral disc space with simplified operations to grasp and release the implant that also permits comfortable wrist positioning for the surgeon during use.

SUMMARY

In one form, an insertion instrument is provided that is configured for controllably inserting an artificial disc device, such as a DNP or TNP spinal implant, a dynamic spacer device, a trial spacer device, or other implant device, between adjacent, superior and inferior vertebrae. The instrument includes an elongate shaft having proximate and distal ends with a longitudinal axis therebetween. Adjacent a distal end of the elongate shaft, the instrument includes a gripping device or mechanism having a holding configuration for securing a portion of the artificial disc device (e.g., an inferior member of the disc device) thereon for insertion into the vertebral space and also a releasing configuration that permits removal of the artificial disc device portion from the instrument. Preferably, the artificial disc device includes an inferior member and a superior member where the inferior member is the portion secured to the gripping mechanism. In one aspect, the instrument includes a handle portion spaced from the distal end that is configured to be comfortably held with a generally neutral wrist position. For purposes herein, a generally neutral wrist position means substantially free of wrist flexion, extension, ulnar deviation, or radial deviation. In one embodiment, the handle portion can be used with a generally neutral wrist position because it is in the form a pistol-grip handle, which is preferably adjacent the proximate end of the instrument.

With such a handle configuration, the instrument provides advantages over prior instruments that include a handle portion aligned along the longitudinal axis of the instrument, such as the prior instruments of Ralph et al., Nichols et al., and Errico et al. described in the background. In use, the prior instruments with handles extending along the longitudinal axis typically require some un-natural wrist positioning in order to secure the artificial disc device thereon or to insert the disc device in a patient during surgery. The instruments provided herein, on the other hand, can be comfortably used generally without un-natural wrist positioning. By using a generally neutral wrist position to hold and use the instrument, the disclosed instruments permit better control thereof when inserting a disc device into a vertebral space, which generally means less damage to surrounding tissue.

In another form, the instrument also includes an actuating mechanism that is coupled between the gripping mechanism and the handle. The actuating mechanism is operable to configure the gripping mechanism adjacent the distal end of the instrument in one of the holding configuration and the releasing configuration. Similar to the handle, the actuating mechanism is also configured to be operated comfortably using a generally neutral wrist position. To this end, the actuating mechanism preferably includes a trigger portion that is configured to move relative to the handle such as being comfortably squeezed by a surgeon to operate the actuating mechanism in order to shift the gripping device between the holding and releasing configuration.

Preferably, the actuating mechanism also includes a pivot connection between the handle and trigger so that the trigger may be actuated by squeezing or pivoting the trigger towards the handle. Such configuration is advantageous because the actuating mechanism, and in particular, the trigger thereof, can also be operated comfortably with the same neutral positioning of the wrist that enables the surgeon to hold the instrument.

In one particular form, the actuating mechanism is preferably capable of switching between the holding and releasing configuration of the gripping device using the same actuating motion of the trigger. In other words, only the single trigger portion is preferably needed to both hold and release the artificial disc device on the distal end of the instrument. Prior instruments, on the other hand, require multiple controls to both hold and release the instrument, which complicates the use of the instrument or necessitates both hands of the surgeon to operate the instrument. The instruments described herein, on the other hand, can secure and release a disc device to the instrument using the same actuating mechanism, and in particular, the same trigger device. In addition, the instrument can secure and release a disc device through the same actuating motion of the single trigger, such as squeezing, which also permits instrument operation with only a single hand of the surgeon. For example, a first squeeze of the trigger configures the gripping device to the holding configuration and a second squeeze of the trigger configures the gripping device to the releasing configuration.

In another embodiment, the instrument also includes a locking device to substantially restrict movement of the artificial disc device about the distal end of the elongate shaft. Preferably, the locking device is aligned with the longitudinal axis of the elongate shaft to permit ease of use by the surgeon's thumb or other finger. Furthermore, with the locking device aligned along the longitudinal axis of the instrument, the locking device does not obstruct the view of the surgeon to the operative site. In one form, the locking device includes a control member that is configured to rotate or turn about the longitudinal axis to shift the instrument between locked and unlocked configurations. Preferably, the locking device also includes a guide member that is arranged to limit over rotation of the locking device. To this end, the guide member includes a stop that limits the turning or rotation of the device. The guide member is advantageous because it provides a positive stop for the locking device and signals to the surgeon that the instrument has locked the artificial disc device to the end of the instrument.

BRIEF DESCRIPTION OF THE DRAWINGS

FIG. 4 is an elevational view of the insertion instrument showing a pistol grip configuration of the handle portion including a trigger coupled thereto and the distal end of the elongate shaft assembly in an initial configuration prior to receiving a disc device;

FIG. 5 is a bottom plan view of the insertion instrument showing a spring mechanism coupled to the trigger;

FIG. 15 is an elevational view of the instrument showing the instrument in a configuration for loading the inferior implant portion (not shown) to the gripping mechanism where the release has been moved to a full open position and the trigger is configured for further squeezing;

FIG. 16 is an elevational view of the distal end of the elongate shaft showing the gripping mechanism configured to receive an implant (not shown) with a latch member having a post thereon being retracted for receipt of the implant;

FIG. 27 is a perspective view of the locking device showing a coil spring member and a selective engagement between the lock knob and coupling member; the lock knob and coupling member are shown disengaged;

FIG. 28 is a perspective view of the lock knob showing a bore extending therethrough having internal threads defined on a portion of an inner surface thereof that has a generally D-shaped profile;

FIG. 29 is a perspective view of the coupling member showing external threading extending completely around the coupling member in one portion thereof and only extending partially around the coupling member in another portion thereof;

DETAILED DESCRIPTION OF THE PREFERRED EMBODIMENTS

Figure 1:
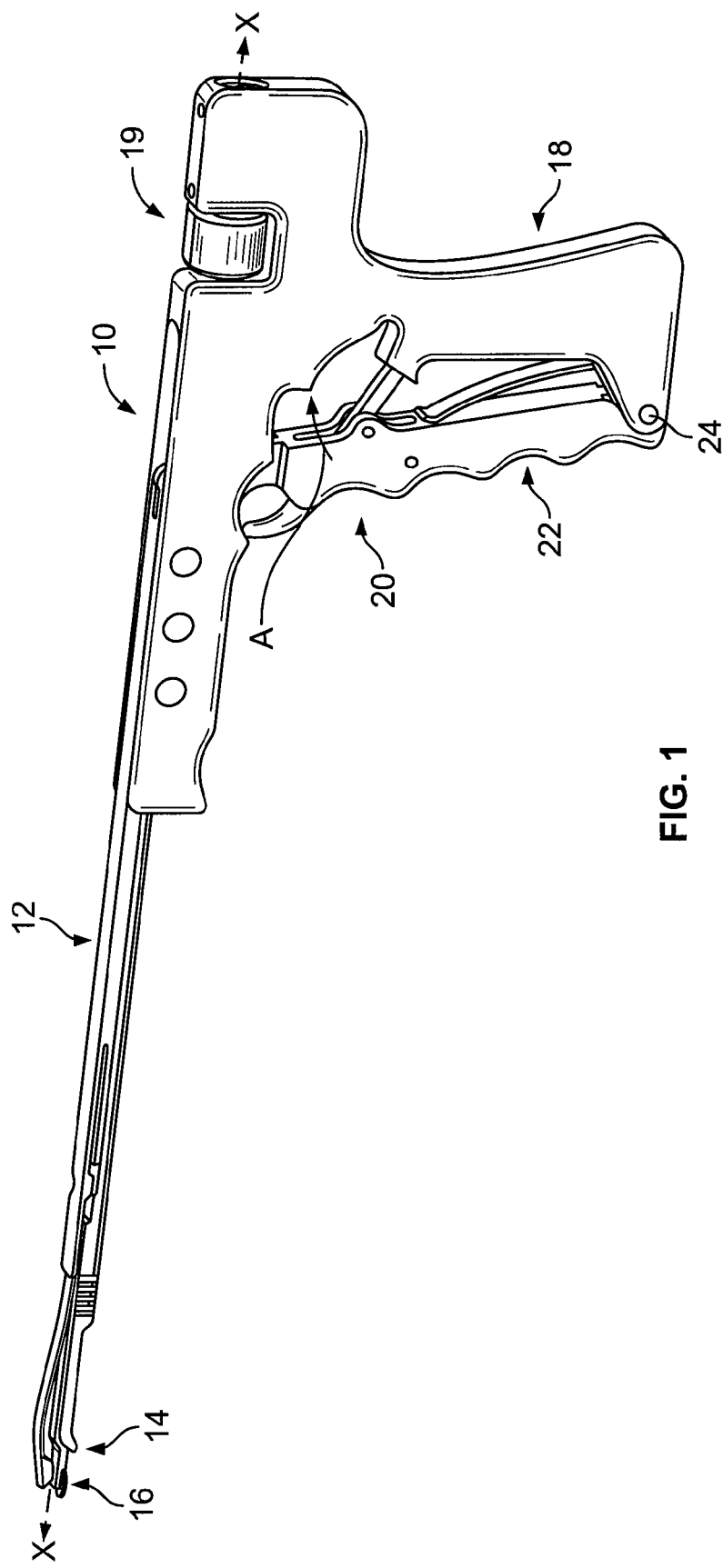
FIG. 1 is a perspective view of one embodiment of an insertion instrument for use with artificial disc devices (not shown) illustrating an elongate shaft assembly having a distal end portion including a gripping mechanism thereon and a handle portion spaced from the distal end that is oriented relative to the elongate shaft such that the handle portion may be held with substantially neutral wrist positioning.
Figure 2:
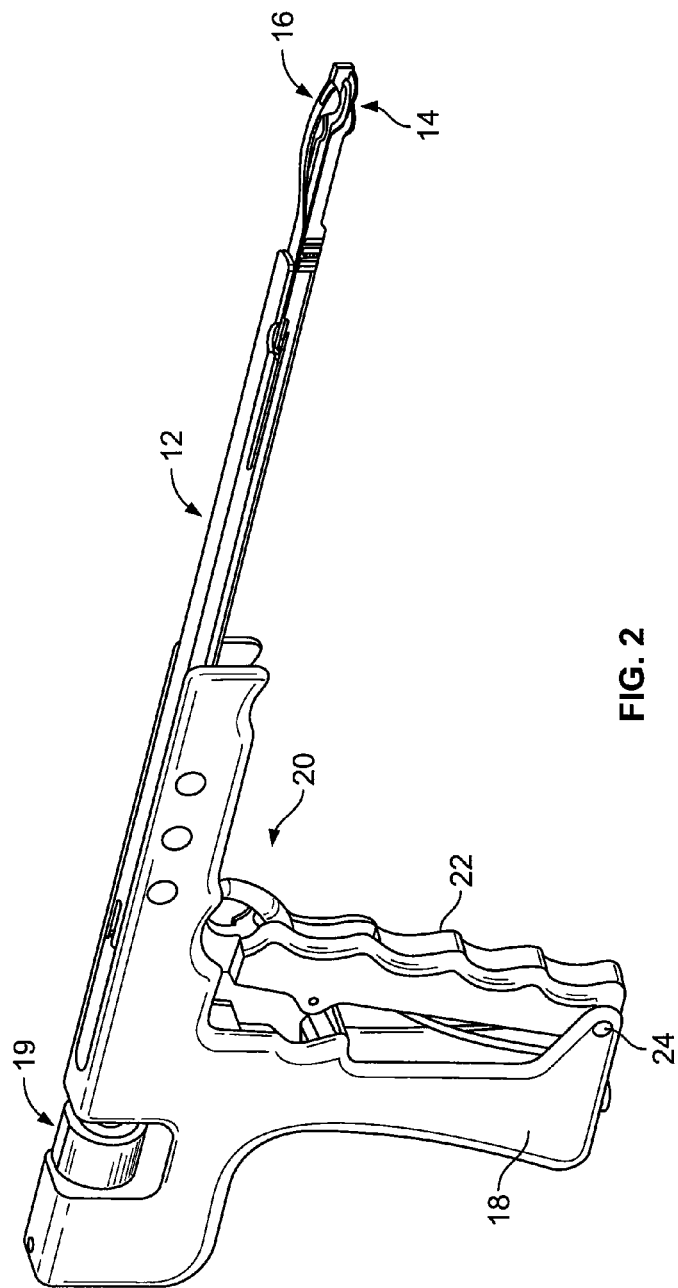
FIG. 2 is a perspective view of the insertion instrument showing the distal end portion thereof for holding the artificial disc device (not shown)
Figure 3:
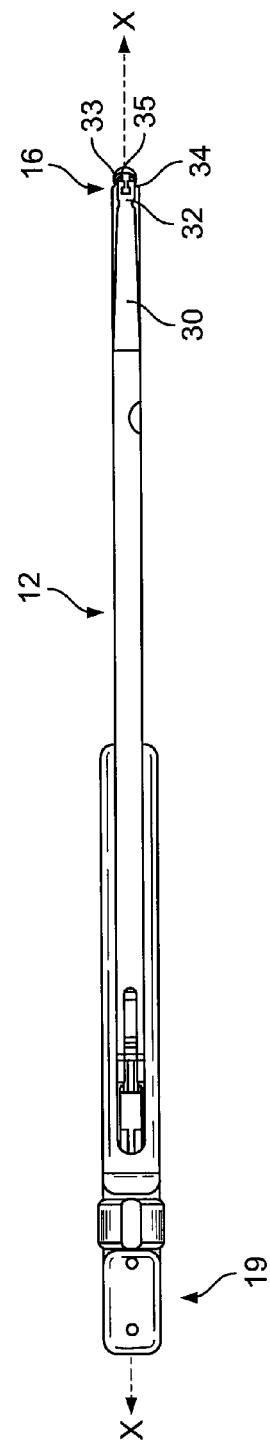
FIG. 3 is a top plan view of the insertion instrument showing the elongate shaft assembly.

Referring to the figures, an insertion instrument 10 for use with artificial disc devices and implants is illustrated. Preferably, the instrument 10 is configured for grasping, orienting, and controllably inserting a disc device between adjacent, superior and inferior vertebrae of a patient. As used herein, disc device refers to a DNP or TNP spinal implant, a dynamic spacer device, a trial spacer device, or other suitable implant device configured for insertion between adjacent vertebrae.

Referring initially to FIGS. 1 to 5, the instrument 10 generally includes an elongate shaft assembly 12 having a distal end portion 14 with a gripping mechanism 16 thereon capable of shifting between a holding configuration for securing the disc device thereon and a releasing configuration for removal of the disc device from the instrument. The instrument 10 also includes a handle portion 18, which is spaced from the gripping mechanism 16, oriented relative to a longitudinal axis X extending along the elongate shaft assembly 12 such that the handle portion 18 may be held with substantially neutral wrist positioning during use thereof.

For purposes herein, a generally neutral wrist position means a wrist substantially free of flexion, extension, ulnar deviation, or radial deviation. In one embodiment, the handle portion 18 can be comfortably used with a generally neutral wrist position because it is in the form of a pistol-grip adjacent a proximate end portion 19 of the elongate shaft 12. In this manner, the instrument 10 provides the surgeon or other user better control thereof when inserting an implant into a vertebral space, which generally means less damage to the surrounding tissue and less time in the operating room.

To operate the gripping mechanism 16, the instrument includes an actuator 20 that is coupled between the gripping mechanism 16 and the handle portion 18. The actuator 20 is operable for shifting the gripping mechanism 16 between the holding and releasing configuration. Preferably, the actuator 20 is capable of shifting the gripping mechanism 16 between the holding and releasing configurations via the same actuation motion of the actuator 20. Similar to the handle portion 18, the actuator 20 is also preferably configured to be comfortably operated using the same generally neutral wrist position.

By one approach, the actuator 20 includes a trigger 22 that is configured to move relative to the handle portion 18 such as being comfortably squeezed by a surgeon using a single hand. Upon one or more actuations of the trigger 22, it is operable to configure the distal end 14 of the elongate shaft assembly 12 or gripping mechanism 16 to grasp and/or release a disc device therefrom. In one form, the trigger 22 is mounted to the handle portion 18 through a pivot connection 24 so that it may be squeezed in the direction of Arrow A to operate the gripping mechanism 16 (FIG. 1). Such combination of the trigger 22 and handle portion 18 in the form of a pistol grip is advantageous because the actuator 20, and in particular the trigger portion 22 thereof, can be operated comfortably with the same neutral positioning of the wrist that enables a user to hold the instrument 10.

In one particular form, the actuator 20 is preferably capable of switching between the holding and releasing configuration of the gripping mechanism 16 using the same actuating motion of the trigger (i.e., squeezing along direction A generally along the longitudinal axis X). In other words, only the single trigger 22 is preferably needed to both hold and release the disc device to the instrument without the need for additional controls as typically found in prior instruments. That is, the instrument 10 can secure and release a disc device through the same actuating motion of the single trigger, such as squeezing, which permits instrument operation with only a single hand of the surgeon. As further described below, a first actuation (i.e., squeeze) of the trigger 22 configures the gripping mechanism 16 into the holding configuration and a second actuation (i.e., squeeze) of the trigger 22 configures the gripping mechanism 16 into the releasing configuration. To facilitate operation of the instrument, the actuator 20 also preferably includes a number of bias elements to shift the actuator between gripping and release an implant. Operation of these bias elements will also be further described below.

Figure 6:
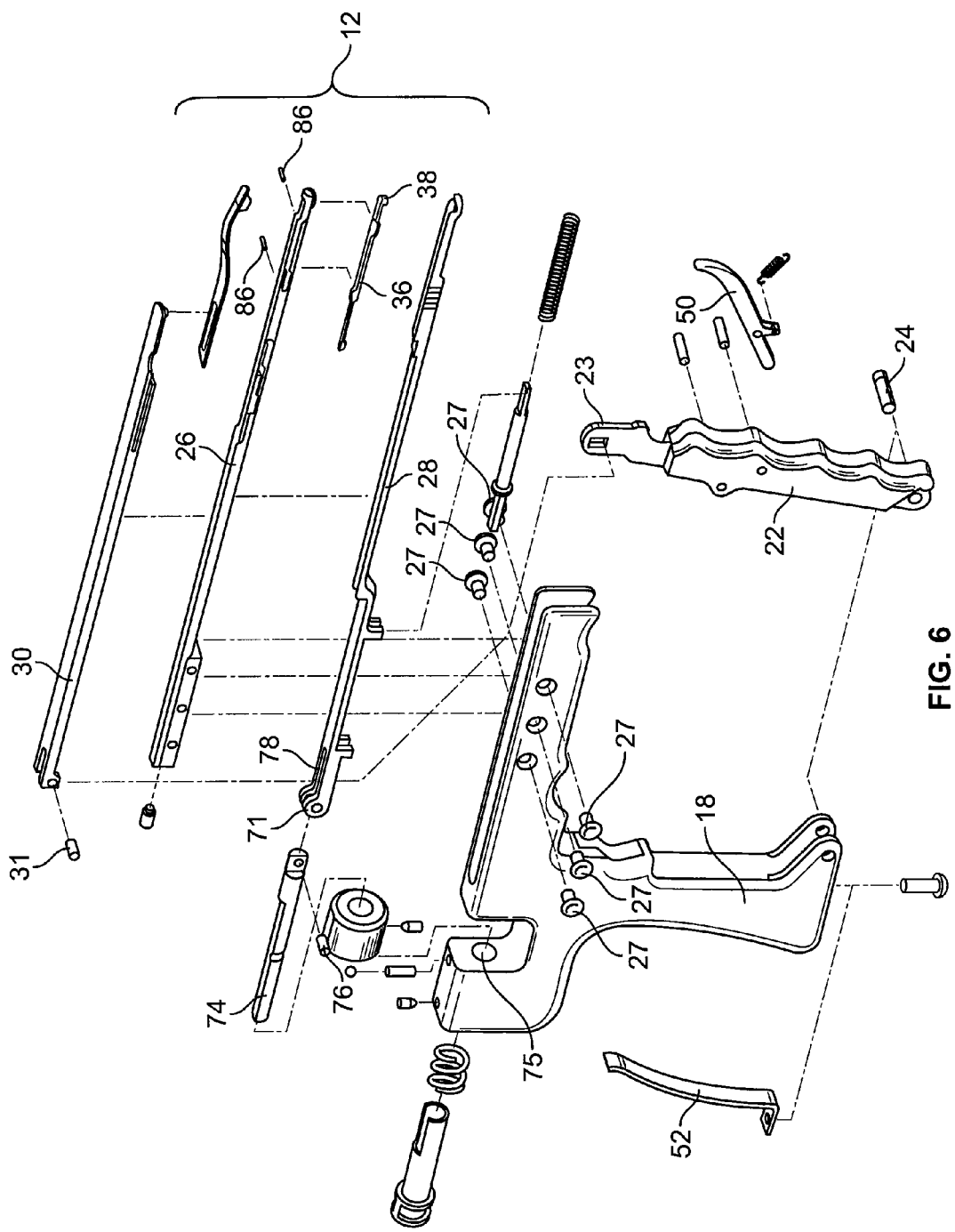
FIG. 6 is an exploded view of the insertion instrument showing an actuation mechanism that includes the trigger connected to the handle portion through a pivot connection and further showing the elongate shaft assembly having a central, fixed portion (fixed to handle portion), a lower slidable portion (slidable relative to the fixed portion), and an upper pivotable portion (pivotable relative to the fixed portion)

Turning to FIG. 6, the elongate shaft assembly 12 of the instrument 10 preferably includes a plurality of members that include both fixed and movable components. In one embodiment, the shaft assembly 12 includes a central, fixed member 26 that is secured to handle portion 18 via one or more fasteners 27. The shaft assembly 12 also includes a lower, slidable member 28 that is configured to shift along the longitudinal axis X relative to the fixed shaft 26 upon actuation of the trigger 22. The shaft assembly 12 also includes an upper, pivotable member 30 that is pivotable relative to the fixed shaft 26 via a pivot 31 mounted to the trigger 22. As illustrated, the upper shaft 30 is coupled to an upper end 23 of the trigger 22 and is also configured to translate along the longitudinal axis X with the pivoting of the trigger 22.

Figure 7:
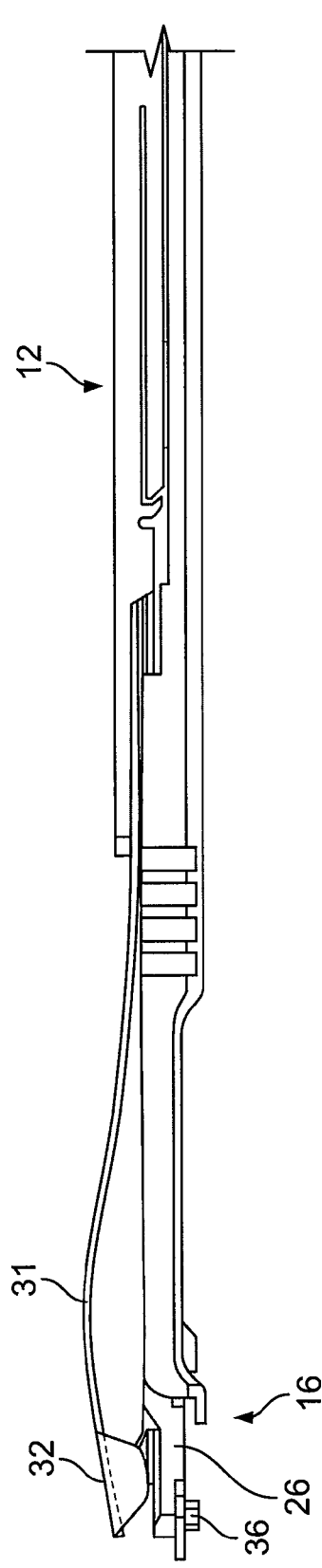
FIG. 7 is an elevational view of the elongate shaft assembly showing the fixed portion, the lower slidable portion, and the upper pivotable portion having a biased holding member.
Figure 8:
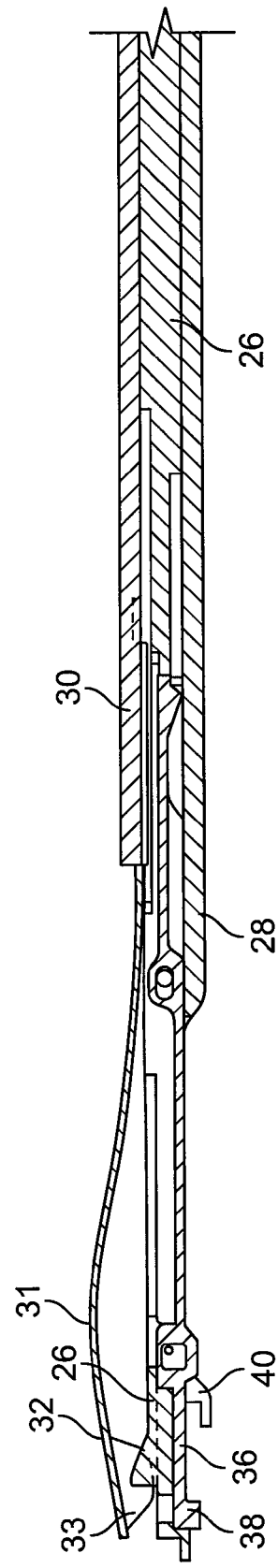
FIG. 8 is a cross-sectional view of the distal end of the insertion instrument showing the gripping mechanism thereon.

The distal end 14 of the elongate shaft assembly 12, which has the gripping mechanism 16 thereon, is illustrated in FIGS. 7 and 8 in more detail. As mentioned above, the gripping mechanism 16 shifts between a gripping configuration where it holds a disc device thereon and a release configuration where it releases a previously held disc device. In the gripping configuration, it holds a superior member of a disc device on the upper pivotable member 30 of the shaft assembly 12 and holds an inferior member of a disc device due to the cooperation of the slidable member 28 and the fixed member 26.

More specifically, the gripping mechanism 16 includes a first portion of a resilient strip member 31 forming a yoke grip that is biased to be bowed upwardly relative to the central fixed shaft 26 of the elongate shaft assembly 12. Preferably, the resilient member 31 is connected to a distal end of the upper pivotable shaft 30. As further described below, the bowed configuration of the resilient member 31 helps orient the superior member of a disc device to extend in a generally transverse or inclined direction relative to the instrument longitudinal axis X in a wedge configuration. In order to grasp the disc device superior member, the resilient member 31 has a grasping claw 32 for engaging a neck or post on the superior member of the disc device (i.e., FIG. 3). In one form, the claw 32 has two laterally, spaced fingers 33 and 34 that form a groove 35 therebetween to secure a disc device post in the groove 35 (i.e., FIGS. 3 and 22).

To hold an inferior member of a disc device, the elongate shaft assembly includes a latch member 36 having a depending post 38 on a distal end thereof. The latch member 36 is in the form of an elongate strip configured to shift between a latching position shown in FIGS. 7 and 8 and a retracted position shown in FIG. 16. In general, the gripping mechanism 16 holds the inferior implant member because the latch post 38 is sized to be received in an aperture defined in the inferior member of the implant. Thereafter, the lower slidable shaft 28 of the shaft assembly 12 then slides forward to abut an outer edge or at least a portion of an outer region of the inferior member of the disc device with a hooked end 40 (FIG. 8) capturing the implant between the post 38 and slidable shaft 28. Operation of the gripping mechanism 16 will be described in more detail below, but the gripping mechanism 16 and operation thereof is similar to that described in U.S. Patent Application Ser. No. 60/822,027, which this application claims priority to and is also incorporated by reference as if reproduced herein in its entirety.

Figure 9:
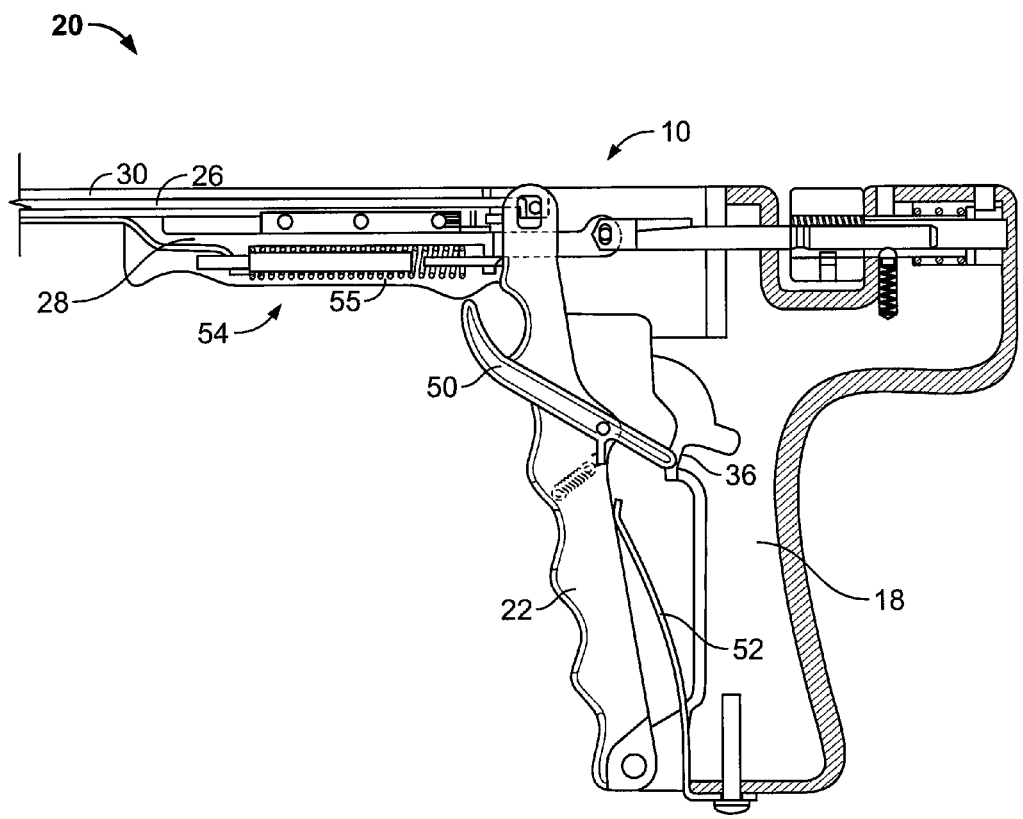
FIG. 9 is a detailed, elevational view of the handle portion showing the trigger portion for being activated or pivoted inwardly towards the handle and a release member in a locked configuration.
Figure 10:
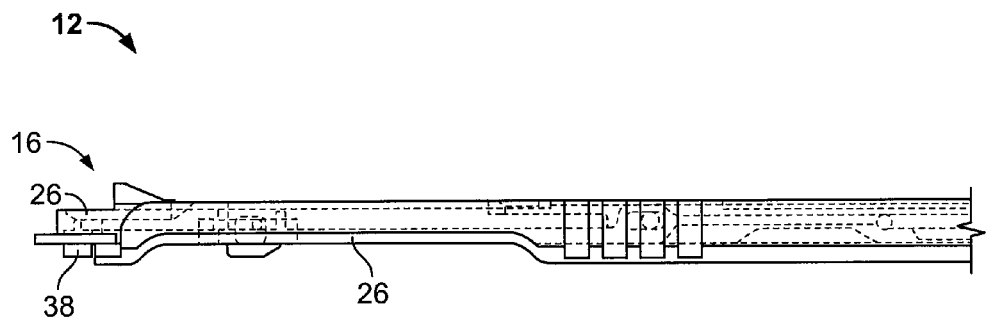
FIG. 10 is an elevational view of the distal end of the insertion instrument showing the gripping mechanism thereon and a latch member for coupling with a disc device (not shown)
Figure 11:
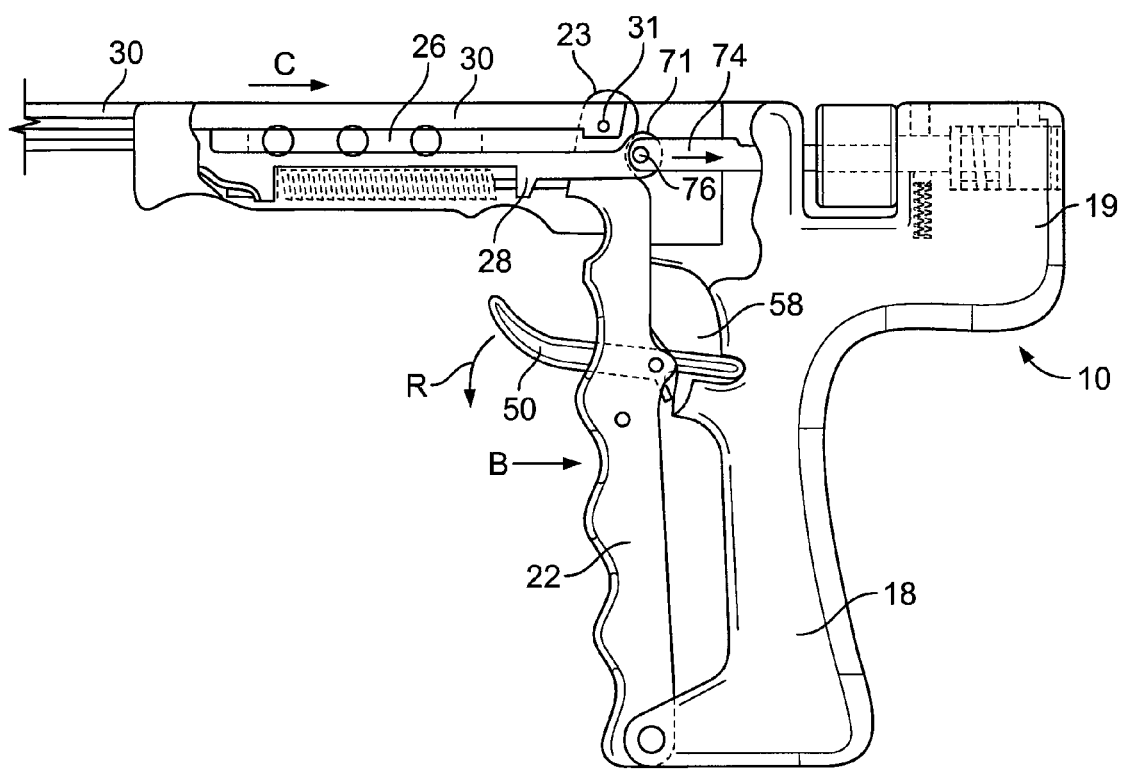
FIG. 11 is a partial, cut-a-way view of the handle portion showing the trigger for being activated or pivoted inwardly towards the handle and the release member in an half-open configuration so that a trigger may be squeezed toward the handle.

Referring to FIGS. 9-11, one embodiment of the actuator 20 is illustrated in more detail. In FIG. 9, the actuator 20 is illustrated as including the trigger 22, a release member 50 that stops or allows actuation of the trigger 22, and a bias element 52 in the form of a leaf spring positioned between the handle portion 18 and the trigger 22 that normally biases the trigger 22 away from the handle portion 18. It will be appreciated, however, that other forms of the actuator 20 are also possible so long as they can be actuated using a generally neutral wrist position.

The actuator 20 further includes a connecting linkage 54 including a bias element 55 in the form of a coil spring coupling the actuator portion in the handle 18 to the lower slidable shaft 28 of the elongate shaft assembly 12. As best shown in FIG. 9, the instrument 10 is in an initial position as it would be received by a surgeon prior to an operation. In this position, the release member 50 is interfering with operation of the actuator 20 because it is abutting a stop surface 56 of the handle 18. In this configuration, the trigger 22 is prevented from being operated by a user. FIG. 10 illustrates the distal end of the elongate shaft 12. In this view, the gripping mechanism 16 is also shown in its initial or stage one position prior to receiving a disc device.

Referring to FIG. 11, to operate the gripping mechanism 16 to grasp a disc device, the release member 50 is first moved to an orientation (Arrow R) that permits operation of the trigger 22. That is, the release member 50 is shifted to a half-open position where it is aligned to be received in a pocket 58 defined in the handle portion 18 so that the trigger 22 may be moved without obstruction. Then, to operate the actuator, the trigger 22 is pivoted (i.e., squeezed) relative to the handle 18 by a user's hand in the direction of Arrow B towards the handle 18.

Figure 12:
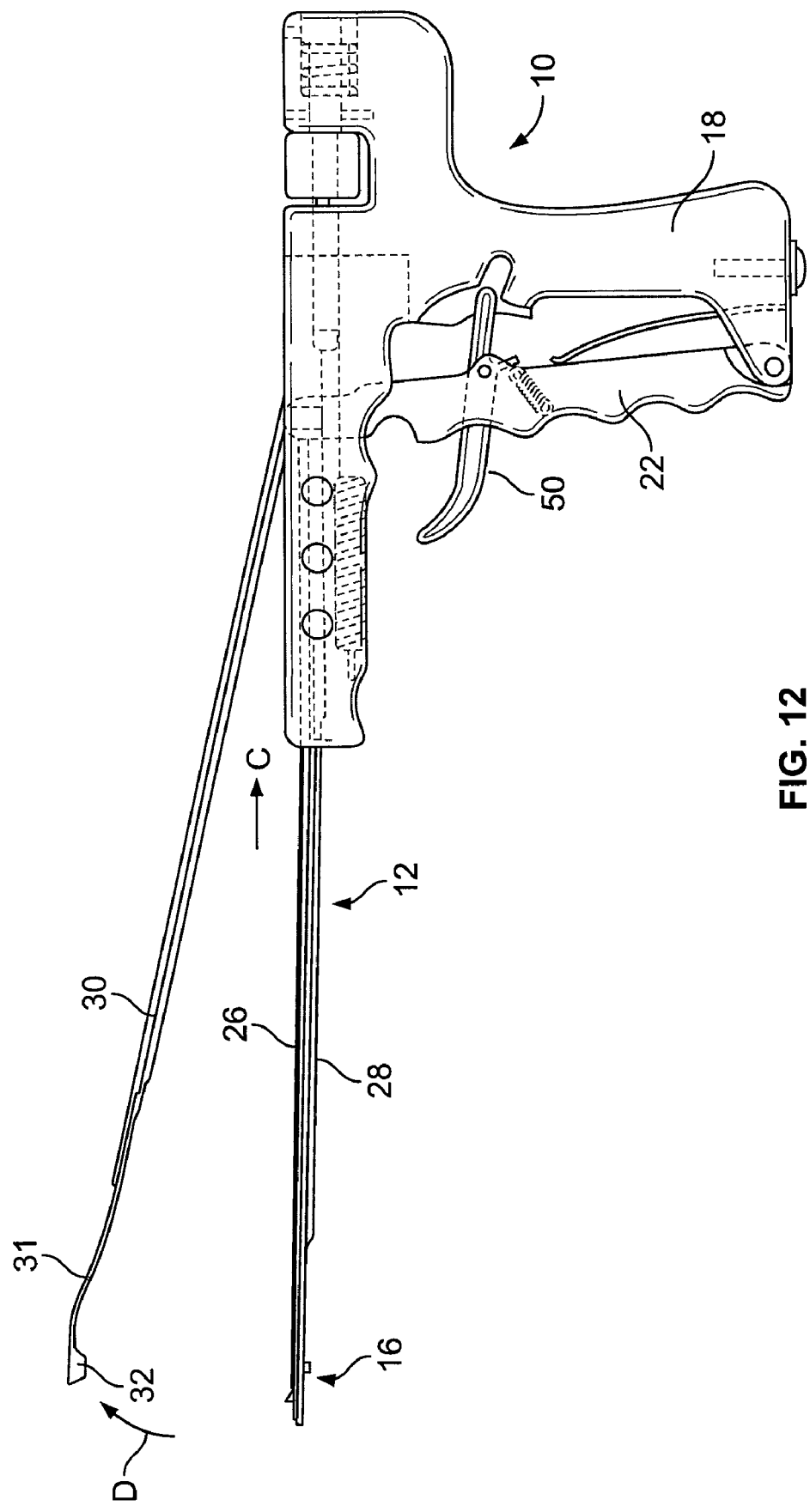
FIG. 12 is an elevational view of the instrument showing the elongate shaft assembly after an initial actuation of the trigger where the upper, shaft portion is pivoted away from the fixed shaft portion.

With such operation, because the upper pivotable shaft 30 of the shaft assembly 12 is connected to the trigger 22 through the pivot 31, it is also shifted rearwardly (Arrow C) upon the squeezing of the trigger 22. With such rearward movement of the shaft 30, it is released from the fixed central shaft 26 and is then free to pivot upwardly (Arrow D) away from the shaft assembly 12 as best shown in FIG. 12. As a result, the claw 32 on the resilient member 31 of the upper shaft 30 is spaced from the shaft assembly 12 and positioned to load a superior portion of an artificial disc device (not shown) on the upper shaft 30.

Figure 13:
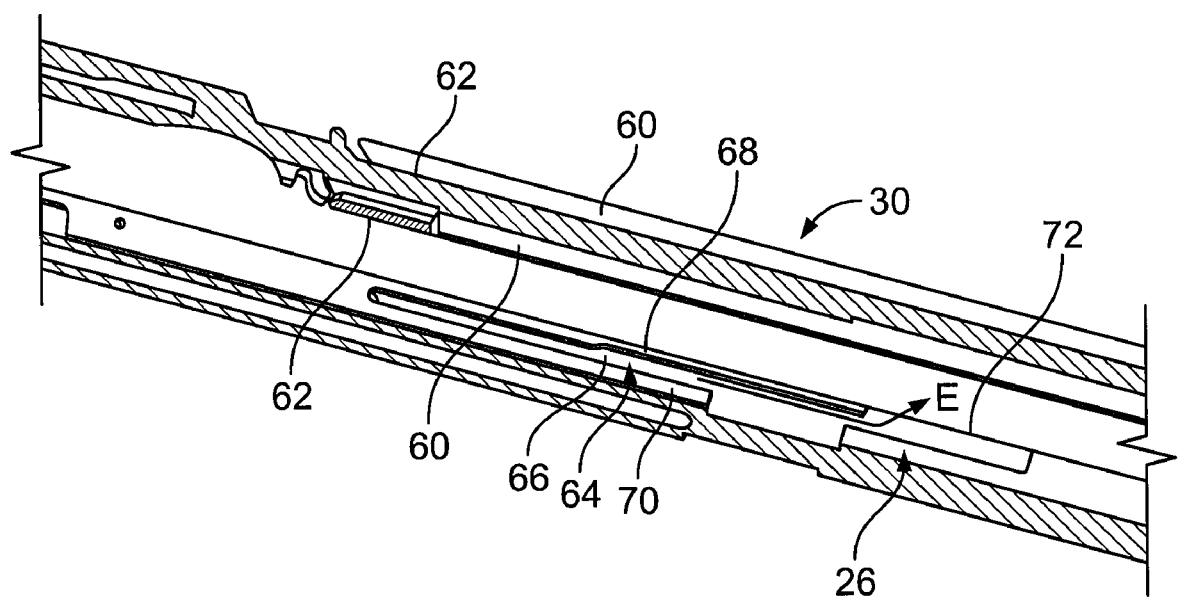
FIG. 13 is an exploded view showing a coupling between an upper, pivotable shaft portion and a fixed shaft portion, the coupling including a track on the fixed shaft portion and a resilient tab portion on the pivotable shaft portion.

Referring to FIG. 13, the pivotable shaft 30 functions as described above because it includes resilient holding arms 60 on opposite sides thereof that have tabs 62 extending orthogonal to the longitudinal axis X of the shaft 12. The tabs 62 are positioned to be received in a recessed track 64 on sides of the fixed shaft 26. Normally, when the pivotable shaft 30 is coupled to the fixed shaft 26 (i.e., prior to actuation of the trigger 22), the tabs 62 are received in a first track portion 66 wherein upper and lower shaft walls 68 and 70, respectively, hold the shaft 30 coupled to the shaft 26 because the tabs 62 are held within the track 64. However, upon the initial actuation of the trigger 22, the upper shaft 30 is retracted rearwardly so that the tabs 62 slide in a corresponding rearwardly direction and eventually are released upwardly via track openings 72 at a rear end of the track 64. As a result, the tabs 62 generally follow Arrow E upon actuation of the trigger 22 to permit the release of the upper shaft 30 from the fixed shaft 26 as previously described and illustrated in FIG. 12.

Figure 14:
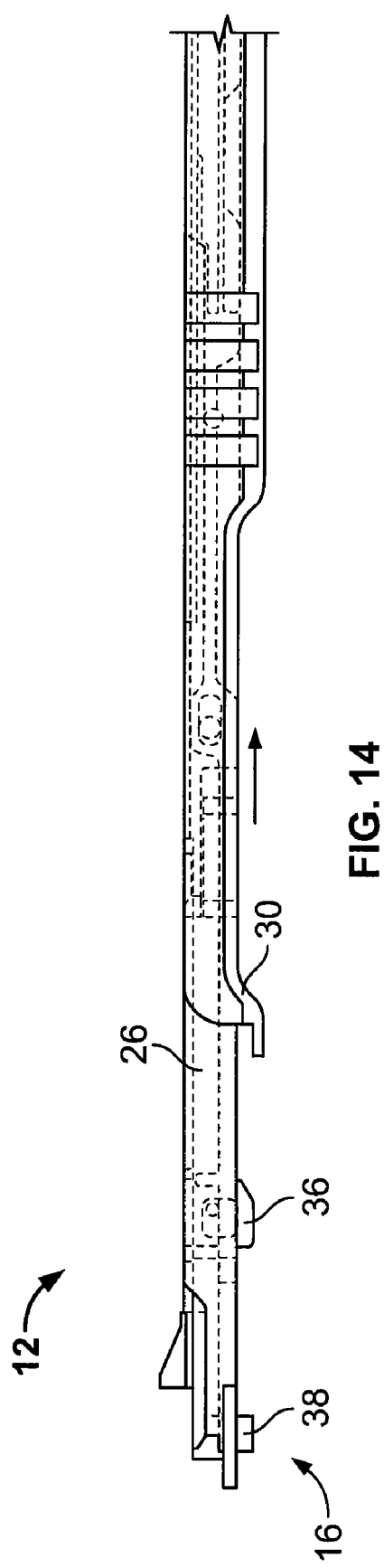
FIG. 14 is an elevational view of the distal end of the insertion instrument showing the gripping mechanism thereon in a second configuration (after a first or initial actuation of the trigger) that is arranged to receive the inferior portion of an artificial disc device (not shown) thereon where the lower, slidable portion of the elongate shaft assembly has been retracted rearwardly relative to the central, fixed shaft by operation of the trigger.

After the first or initial actuation of the trigger 22 as described above, the distal end 14 of the insertion instrument 10 shifts the gripping mechanism 16 thereon to a second or stage two configuration, which is arranged to receive the inferior portion of an artificial disc device (not shown) thereon as best shown in FIG. 14. In this configuration, the lower, slidable shaft 28 of the elongate shaft assembly 12 has been retracted or shifted rearwardly relative to the central, fixed shaft 26 a predetermined amount via the operation of the trigger 22 as described above.

More specifically, the lower shaft 28 is shifted rearwardly due to the interaction of the trigger 22 and a locking shaft 74, which is best described in regard to FIGS. 6 and 11. That is, a proximate end 71 of the slidable shaft 28 is coupled to the locking shaft 74 via a linkage or lock pin 76. The locking shaft 74 is configured to slide along the axis X of the shaft assembly 12 within a bore 75 extending through the proximate end portion 19 of the handle portion 18. The upper end 23 of the trigger 22 extends through a slot 78 formed in the proximate end 71 of the shaft 28. Therefore, upon operation of the trigger 22, the upper end 23 of the trigger 22 abuts the locking shaft 74 and shifts it rearwardly. Because the locking shaft 74 is coupled to the lower shaft 28 via the linkage 76, the rearwardly shifting of the locking shaft 74 also shifts the shaft 28 in the same direction to the retracted position generally illustrated in FIG. 14 described above.

In one embodiment, to load the inferior portion of an implant to the gripping mechanism 16, the release member 50 is pivoted to a full open position where it is further shifted along the direction of Arrow A (FIG. 15). The trigger 22 is then squeezed further or a second time to configure the instrument 10 to a third or stage three configuration best shown in FIGS. 15 and 16 where the latch member 36 is retracted in the shaft assembly 12 to permit easy insertion of the disc device inferior member to the gripping mechanism 16.

Figure 17:
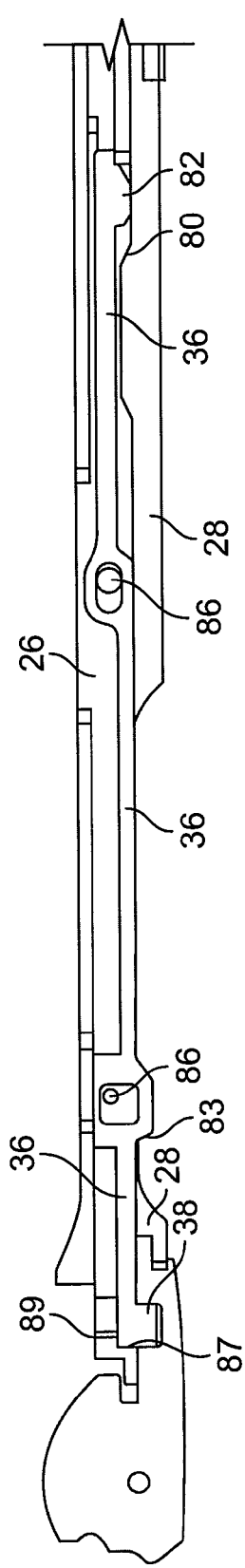
FIG. 17 is cross-sectional view of the distal end of the instrument showing the latch member in a received configuration after an implant has been inserted on the distal end of the elongate shaft assembly.
Figure 18:
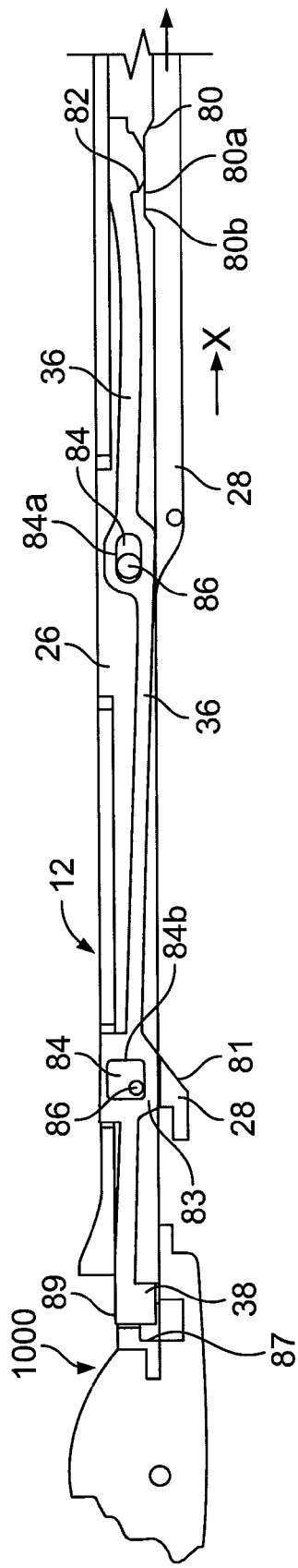
FIG. 18 is cross-sectional view of the distal end of the instrument showing the latch member in a retracted configuration.

By one approach, the latch member 36 is retracted relative to the shaft assembly 12 due to the rearwardly sliding of the lower shaft 28 upon operation of the trigger 22 as best shown in the views of FIGS. 17 and 18. For example, the latch 36 is shown in a down position and the lower shaft 28 positioned forwardly prior to the operation of the trigger 22 in FIG. 17. Upon operation of the trigger 22, the lower shaft portion 28 slides rearwardly so that inclined shaft engagement surfaces 80 and 81 abut inclined latch contact surfaces 82 and 83, which generally cams the latch 36 rearwardly and upwardly so that the post 38 is withdrawn in the shaft assembly 12 as shown in FIG. 18. In a preferred approach, inclined surfaces 80 and 81 do not abut their corresponding latch surfaces 82 and 83 at the same time, but contact each other sequentially through a series of steps. First, the surface 80 of keel 80a cams and lifts surface 82 to position the latch 36 to be retracted where the surface 82 is riding on the top 80b of keel 80a (FIG. 18). As a result, surface 81 will then cam against surface 83 resulting in the latch 36 being moved in the X direction once an upper edge 89 of post 38 clears a step 87 in the tip of the fixed member 26, which permits the post 38 to retract into the fixed member 26. To facilitate such motion, the latch 36 may flex or bend, as exemplified in FIG. 18. When the latch 36 is in the down position of FIG. 17, the abutment of the upper edge 89 of the post 38 into the step 87 generally prevents inadvertent movement of the post 38. To facilitate such camming of the latch 36, it preferably includes openings 84 that extend orthogonal to the direction of the elongate shaft axis X though which alignment pins 86 extend. As shown, a rearward opening 84a is generally elongate to permit shifting of the latch 36 along the elongate shaft axis X while the forward opening 84b is generally rectangular or square to permit both shifting and camming of the latch 36. The size of the openings 84 generally permit the amount of shifting of the latch 36.

Figure 19:
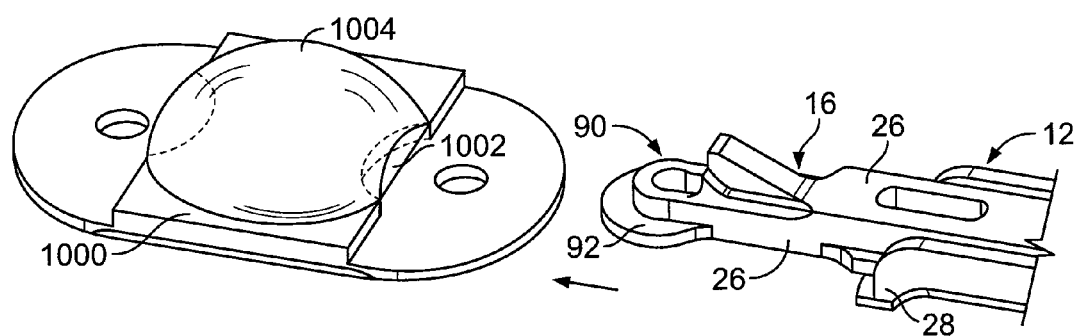
FIG. 19 is a perspective view showing an exemplary inferior implant portion being positioned to engage a tip of the gripping mechanism where an annular flange on the tip of the gripping mechanism is configured for receipt in an undercut slot in a central dome portion of the implant.
Figure 20:
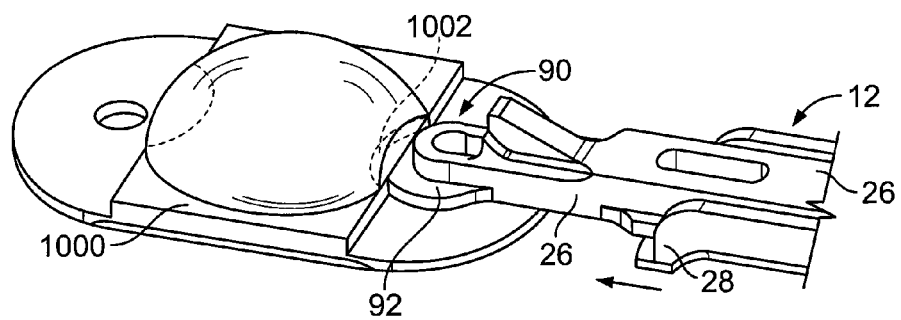
FIG. 20 is a perspective view showing the annular flange fully engaged with the inferior implant undercut slot.

Turning to FIGS. 19-21 and 21A, an exemplary inferior member 1000 of a disc device is shown being secured or mounted to a tip 90 of the gripping mechanism 16. In FIG. 19, the actuator 20 has been activated by operation of the trigger 22 through stages one and two to prepare the gripping mechanism 16 for receipt of the disc device member 1000. In this form, the tip 90 of the gripping mechanism 16 includes an annular flange 92 for being received in an undercut slot 1002 of a central dome portion 1004 of the implant 1000. Because the latch 36 has been retracted to the position of FIG. 18, the implant 1000 is easily coupled to the tip 90 of the gripping mechanism 16 as shown in FIG. 20, where the annular flange 92 is fully engaged with the inferior implant undercut slot 1002. At this point, the lower shaft 28 is still disengaged from the implant 100. The initial positioning of the implant 1000 is preferably undertaken while the trigger 22 is continually being squeezed; however, if desired, the trigger 22 can be squeezed once to release the upper shaft 30 and then squeezed a second time to position the lower shaft 28 for holding the implant 1000.

Figure 21:
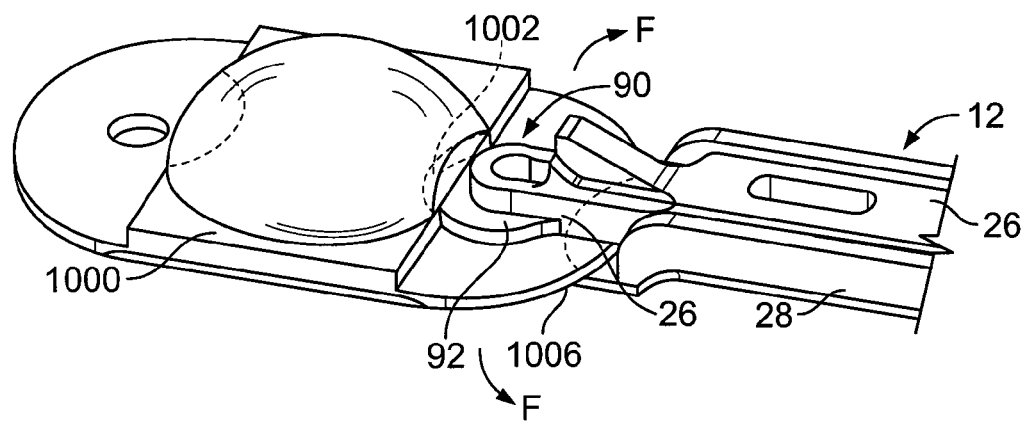
FIG. 21 is a perspective view showing the gripping member after release of the trigger that allows the latch to be inserted into a bore in the implant.
Figure 21A:
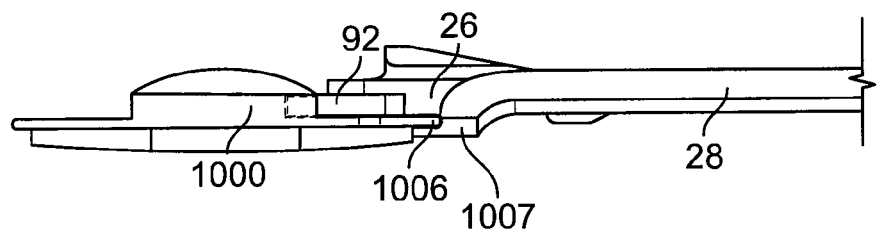
FIG. 21A is an elevational view of the gripping member and implant of FIG. 21.

Once the annular flange 92 is positioned in the undercut slot 1002, the trigger 22 is released to allow the lower, shaft 28 to slide forwardly generally due to the compression of the coil spring 55 by the trigger 22 being pivoted away from the handle 18 by the leaf spring 52. As a result, the lower shaft 28 also slides forwardly where the hook portion 40 abuts against an outer edge 1006 of the implant 1000 as best shown in FIG. 21, and preferably abuts an undercut groove 1007 below the implant outer edge 1006 (FIG. 21A). The forward sliding of the shaft 28 also cams the latch 36 back to its original position where the post 38 is then received in a hole defined in the implant member 1000.

At this point, the implant 1000 is still positionable relative to the tip 90 and can be translated left or right relative to the tip 90 (i.e., Arrows F) for passive steering of the implant if so desired in order to orient the implant for insertion into a patient. Alternatively, the instrument 10 can also be combined with an active steering mechanism, such as the active steering systems described in Application Ser. No. 60/822,027, which is hereby incorporated by reference as if reproduced herein in its entirety.

Figure 22:
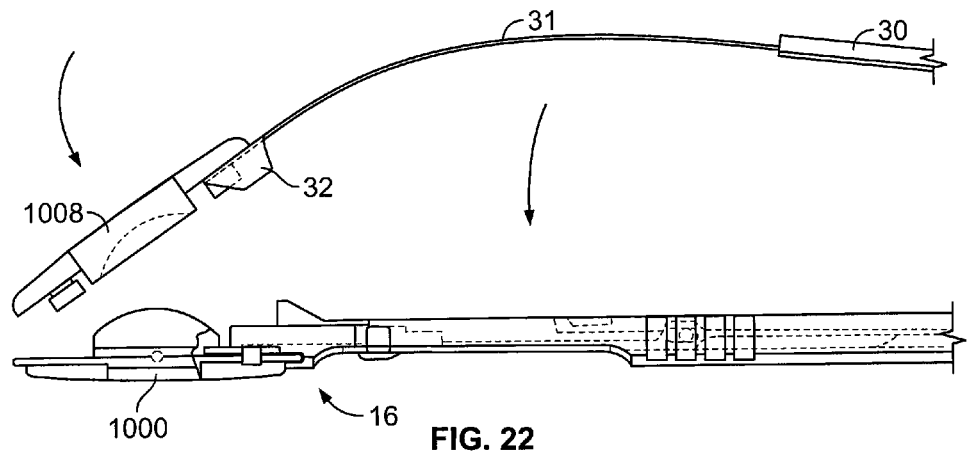
FIG. 22 is a perspective view showing the distal end of the instrument with the upper shaft portion being pivoted downwardly towards the fixed shaft with an exemplary superior implant secured to the distal end of the upper shaft.
Figure 23:
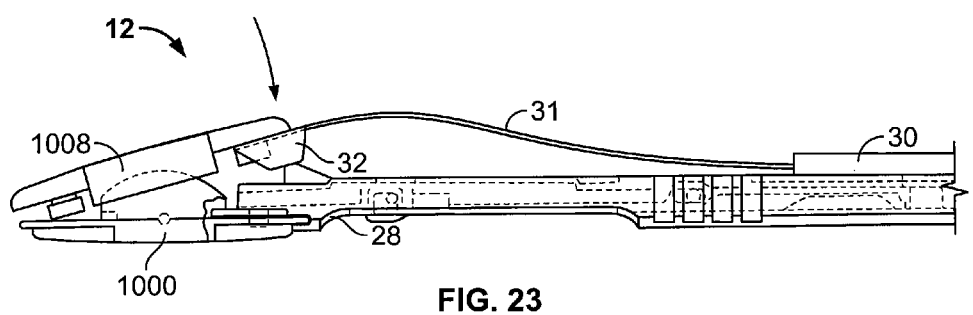
FIG. 23 is a perspective view showing the distal end of the instrument with the upper shaft portion secured to the fixed shaft portion to position the superior implant in a wedge configuration relative to the inferior implant.
Figure 24:
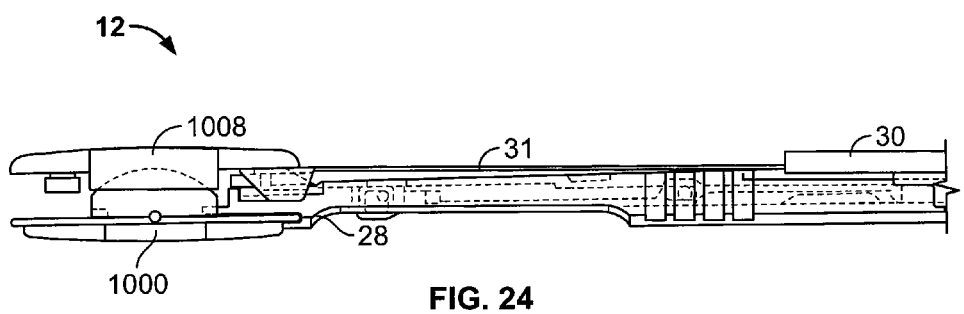
FIG. 24 is a perspective view of the distal end of the instrument showing the positioning of the implant portions after being inserted into a vertebral space between two adjacent vertebrae (not shown) with the superior and inferior implant portions being generally parallel to each other.

Thereafter, the upper shaft 30 is then pivoted downwardly toward the shaft assembly 12 in order to couple the inferior 1000 and superior 1008 implant members into the preferred wedge configuration for implantation as best shown in FIGS. 22 and 23. Once pivoted down towards the shaft assembly 12, the upper shaft 30 is secured to the fixed shaft 26 because the tab portions 62 of the shaft 30 (FIG. 13) are snap-fit into a forward portion 66 of the elongate track recess 64 in the fixed shaft 26. To this end, the tabs 62 are formed on resilient strips configured to shift or flex outwardly orthogonal to the longitudinal axis X to permit the tabs 62 to clear the upper track wall 68 and then shift back to its original position when the tabs 62 are received in the track 64. Once the upper shaft 30 and the fixed shaft 26 are coupled in such a manner, the biased strip member 31 will position the upper implant member 1008 in the wedge configuration relative to the lower implant member 1000 as best shown in FIG. 23. The implant members 1000 and 1008 are then configured for insertion into a vertebral space. Once inserted, the implant portions 1000 and 1008 are oriented generally parallel to each other as shown in FIG. 24 due to the compression forces from the superior and inferior vertebrae (not shown). Once inserted, the trigger 22 can be actuated again to remove the gripping mechanism 16 from the implant as the surgeon pulls back on the handle 18.

Figure 25:
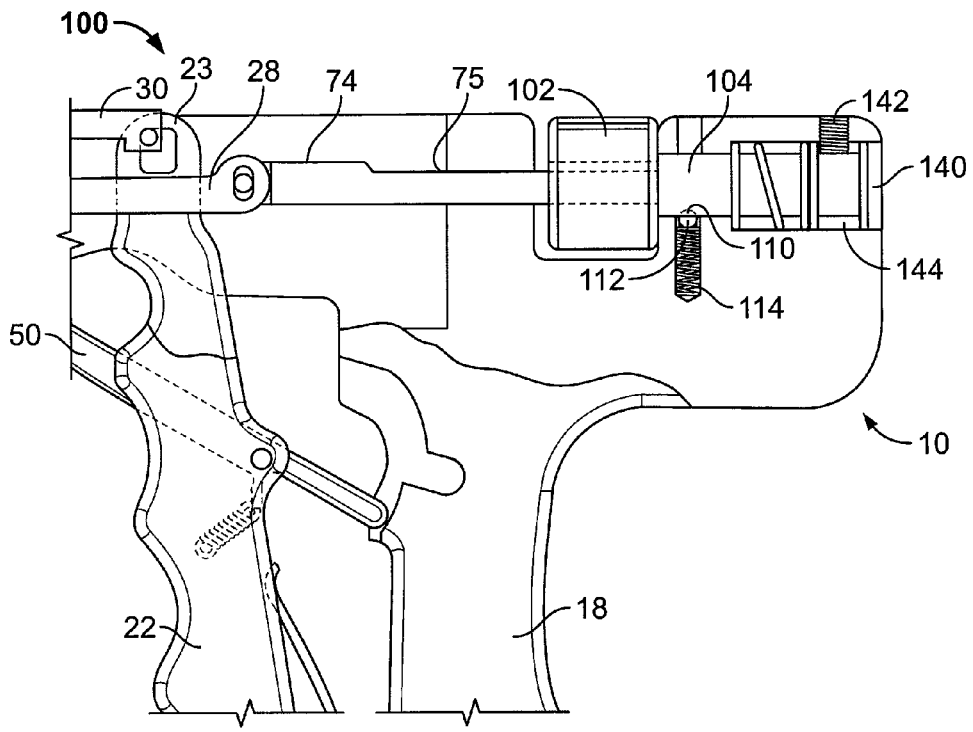
FIG. 25 is a partial cut-a-way view of the locking device showing a lock knob, a coupling member, and a guide tube that is configured to limit the turning or rotation of the lock knob.
Figure 26:
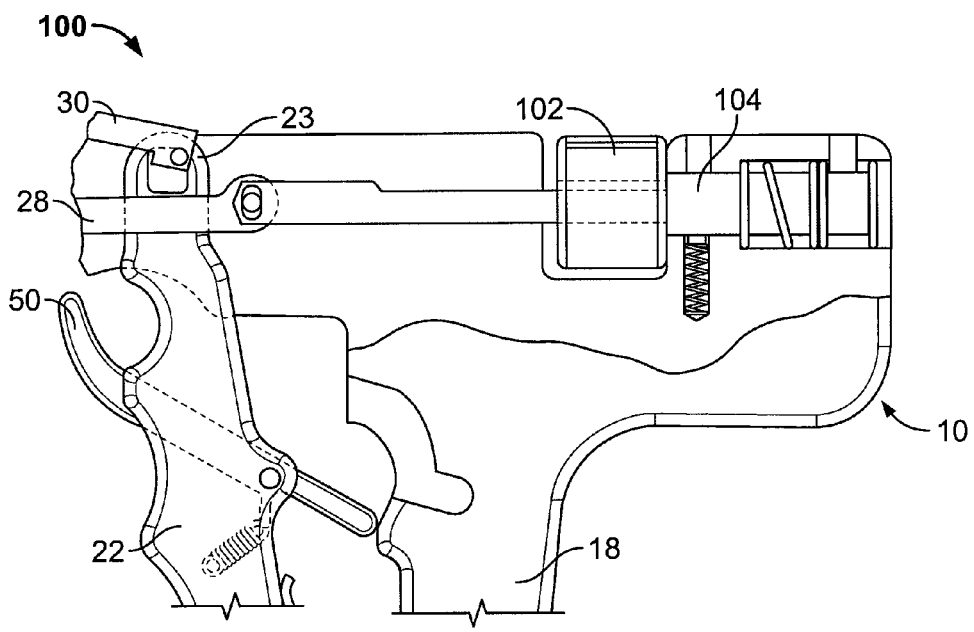
FIG. 26 is a partial cut-a-way view showing portions of the actuating mechanism and a locking device thereof.

Once the implant 1000 is coupled to the tip 90 of the gripping mechanism 16 as described above and optionally oriented left or right (if desired), the disc device is then preferably locked to the instrument 10 prior to insertion into a patient. In a preferred approach, the implant 1000 is locked generally straight along the shaft axis X. Turning to FIG. 25, one form of a locking device 100 is illustrated in more detail.

Preferably, the locking device 100 is positioned and configured so that it can also be operated while the user continues to hold the instrument handle 18 using the generally neutral wrist position. For example, the locking device 100 is positioned so that in some cases the thumb of the users' hand that is grasping the handle 18 can also be used to shift the locking device 100 between a locked and unlocked configuration. (However, the user's other hand may also be used for assistance if the locking force are high.) When locked the locking device 100 prevents further operation of the actuator 20, generally prevents further rotation or steering of the disc device relative to the elongate shaft 12, and also generally fixes the disc device to the instrument 10. In one form, the locking of the instrument 10 is accomplished by turning a lock knob 102 about the shaft longitudinal axis X so that the locking shaft 74 extending between the locking device 100 and the actuating mechanism 20 is restrained from movement. By one approach, the locking is accomplished by turning the lock knob 102 less than one revolution, preferably, less than about 270°.

Referring to FIGS. 25-32, one embodiment of the locking device 100 is illustrated in more detail. As mentioned above, the locking device 100 includes the lock knob 102 for being turned relative to the longitudinal axis X to both lock and unlock the instrument. The locking device 100 also includes the previously described lock shaft 74, which is restrained against translation upon the lock knob 102 being turned. The locking device 100 further includes a guide member 104 that is configured to limit the turning or rotation of the lock knob 52 to less than one revolution. As best shown in FIG. 27, the guide member 104 is a generally elongate cylindrical tube extending along the shaft longitudinal axis X and is coupled to the lock knob 102 via a set screw 106 extending through a bore 108 in the lock knob (FIG. 28) to fixes the lock knob 102 to the guide tube 104. In this manner, the guide tube 104 moves or turns together with the lock knob 102.

To provide indication that the lock knob 102 is in the un-locked configuration, the guide tube 104 preferably includes a recess 110 (FIG. 31) on one side thereof that is configured to positively receive a detent 112, which is biased upwardly into contact with the guide tube 104 by a bias element 114, such as a coil spring. Therefore, when a user is turning the lock knob 102 in the unlocking direction, they will generally know how far to turn the knob 102 because as the detent 112 is positively received in the recess 110, the user will receive an audible or tactile indication that the knob/ guide tube assembly is in the unlocked position.

The lock device 100 is operable to lock the gripping mechanism 16 because it has a selective engagement with the lock shaft 74, which when in a locked engagement pushes the lower shaft 28 tightly against the inferior implant lower edge 1006 and, preferably, undercut groove 1007. To this end, as best shown in FIG. 28, the lock knob 102 defines a bore 120 extending therethrough. The bore 120 has internal threading 122 defined on a portion 124 of an inner surface 126 of the bore 120. As shown, the bore 120 has a generally D-shaped profile that is configured to cooperate with a similar D-shaped profile on the lock shaft 74 as will be further described below. The internal threading 122 forms part of the selective engagement between the knob 102 and the lock shaft 74.

Turning to FIG. 29 the lock shaft 74 and another portion of the selective engagement is illustrated in more detail. Preferably, the lock shaft 74 is a generally cylindrical, elongate member having external threading 130 on at least a portion thereof and no threading on another portion 132 thereof. As shown, the lock shaft 74 has a D-shaped profile with a curved or arcuate portion 134 and a flat portion 131. In particular, the external threading 130 extends partially around the lock shaft 74 such as on the curved D-shaped portion 134. With such configuration, the partial threading 130 of the lock shaft 74 permits the selective engagement with the partial threading 122 of the lock knob bore 120 in order to lock the instrument when both partial threadings 122 and 130 are mated. That is, for example, when the lock knob 102 is turned about the longitudinal axis X of the instrument 10 (with a user's thumb for example) so that the threading 122 of the knob 120 is threadably mated with the threading 130 of the partial threading portion 134 of the lock shaft the instrument is locked. In this configuration, the instrument 10 is locked because the mating of the threads 122 and 130 prevents further operation of the trigger 22. The implant coupled to the distal end of the shaft 12 is also restrained from movement because the lock shaft 74 is translated towards the distal end of the shaft assembly 12, which also translates the shaft 28 into a tight engagement with the implant inferior member 100 to restrain it from motion relative to the elongate shaft 12.

To unlock the instrument 10, the lock knob 102 is turned about the longitudinal axis X in a reverse direction. When unlocking the lock device 100, the threading 122 of the knob bore 120 is unmated from the threading 130 of the lock shaft portion 132 so that the flat portion 131 of the D-shaped lock shaft 74 and flat portion 125 of the lock knob bore 120 correspond with each other to permit the shaft 74 to translate through the bore 120. The artificial disc device in the gripping mechanism 16 is then generally free to move or pivot relative the elongate shaft and be removed therefrom because the shaft 28 is no longer tightly compressed against the implant lower edge 1006 and, preferably, against undercut groove 1007. Such movement is possible because, in the unlocked position, the lock shaft 74 is generally free to translate or slide along the longitudinal axis X through the lock knob bore 120 because there is no mating between the corresponding threading 122 and 130.

Figure 30:
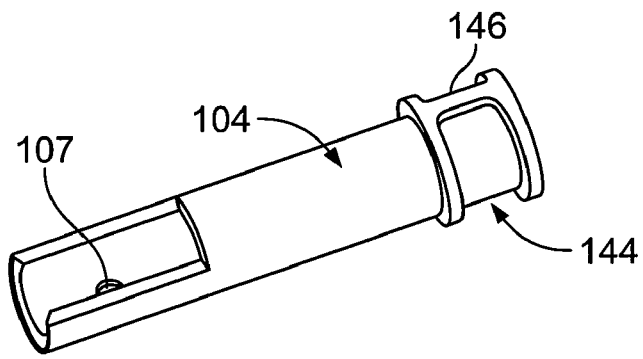
FIG. 30 is perspective view of the guide member that is arranged and configured to limit the turning of the lock knob showing a bore positioned to receive a set screw for securing the guide member to the handle.
Figure 31:
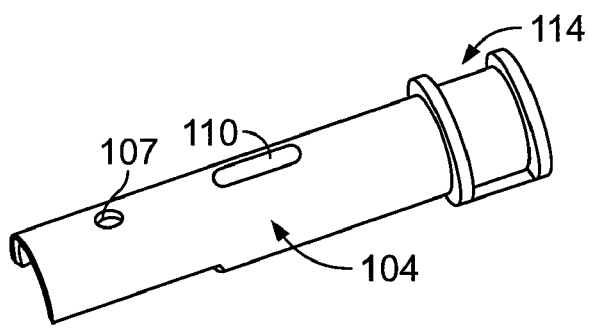
FIG. 31 is a perspective view of the guide member showing an annular channel on a distal end thereof that has a stop portion thereon that engages a protrusion extending through the handle upon rotation of the guide member and lock knob assembly to limit turning or rotation thereof.

In one aspect, the lock knob 102 is turned less than about one revolution or less than about 270° to mate and un-mate the threads 122 and 130. To this end, the turning of the lock knob 102 is preferably limited by the cooperation of the guide tube 104 with the locking knob 102. FIGS. 30 and 31 are perspective views of the guide tube; comparing these views to FIGS. 25 and 27, it can be seen how the guide tube 104 limits turning of the lock knob 104. It will be appreciated, however, that other mechanisms can be employed to limit turning or rotation of the lock device.

As previously discussed, the guide tube 104 is joined to the lock knob 102 via the set screw 106, which is received through a bore 107 in the guide tube 104 so that the guide tube 104 turns as an assembly along with the lock knob 102. The guide tube 104 is inserted through an opening 140 in the instrument handle 18 so that it is generally positioned along the shaft axis X. In this manner, the guide tube 104 is configured for being turned within the opening 140 in cooperation with the turning of the lock knob 102. However, the guide tube 104 is preferably restricted from turning a full revolution via a stop mechanism. For example, a protruding member 142, such as a set screw, pin, protrusion, or the like extends through the handle portion 18 and into an annular channel 144 in the guide tube 104. The channel 144 includes a stop 146 thereon (FIG. 30) that is positioned to engage the protrusion 142 upon a predetermined turning or rotation of the guide tube 104 and lock knob 52 assembly to limit turning or rotation thereof. That is, when the protrusion 142 contacts the guide tube stop 146, the lock knob 102 is substantially hindered from further rotation. In this manner, the locking device 100 limits over rotation thereof that could potentially damage the instrument 10.

Figure 32:
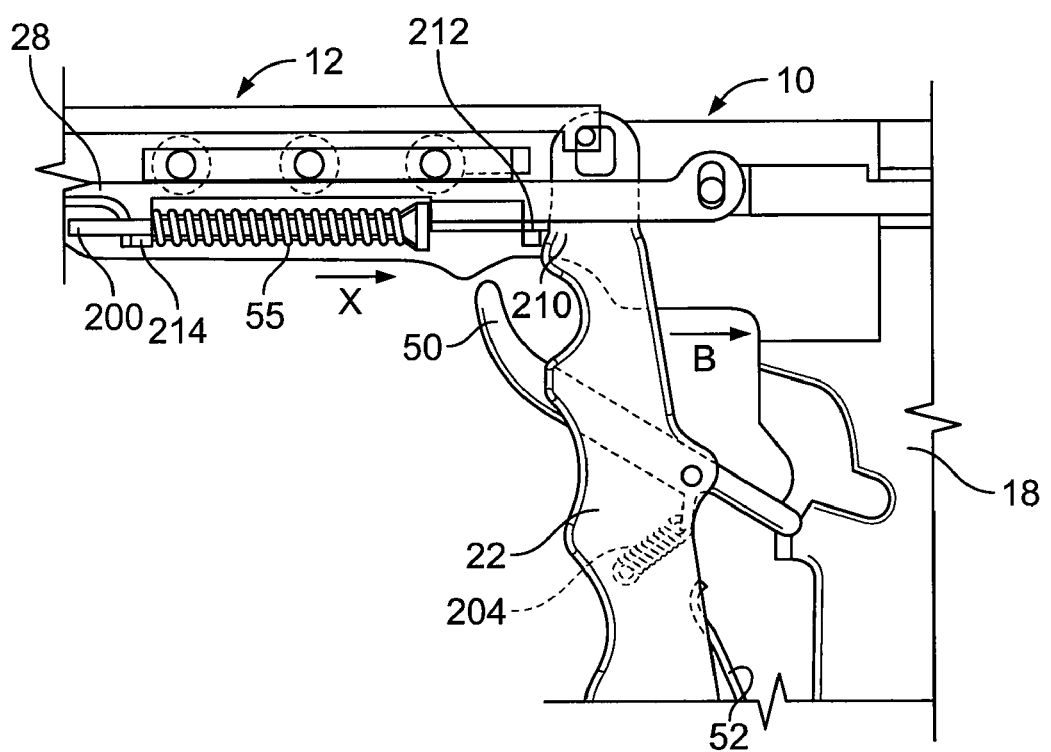
FIG. 32 is an elevational view of the instrument showing the actuating mechanism with the coupling member joined to the lower shaft portion and a bias member that biases the lower shaft portion forwardly.

The instrument also preferably includes a number of additional bias elements to facilitate ease of instrument operations. For instance, as best shown in FIG. 32, a plunger shaft 200 and the bias element 55 are illustrated as being operative for providing a forward motion of the sliding shaft 28 along the shaft axis X. That is, the plunger shaft 200 and the compression of the spring 55 are configured upon release of the trigger 22 to apply a forwardly directed force along axis X to the sliding shaft 28 that shifts the shaft 28 forwardly. For example, upon releasing the trigger 22, the bias element 52 helps bias the trigger into an un-activated direction. At the same time, an upper end 210 of the trigger 22 abuts an end 212 of the plunger shaft 200 which loads or applies a compression force to the spring 55 that shifts the sliding shaft 28 forwardly when the spring 55 applies the force to abutments 214 of the sliding shaft 28. Optionally, the actuator 20 also includes a bias element 204 coupled to the release member 50. The bias element 204 is configured to bias the release member 50 into the locked position as shown in FIG. 32, when not being activated by the user.

As discussed above, the instrument 10 is advantageous because it provides for grasping an implant, locking the implant relative to the instrument, inserting the implant into an intervertebral space, unlocking the instrument, and removing the implant using a generally neutral wrist position and, preferably, only a single actuation control that can also be operated using a generally neutral wrist position. Because the instrument 10 preferably includes the handle portion 18 in the form of a pistol grip and includes the locking device 100 adjacent the pistol grip, the user can operate and lock the instrument 10 in some instances using the same hand, which frees the other hand for other surgical tasks.

While there have been illustrated and described particular embodiments of the insertion device, it will be appreciated that numerous changes and modifications are possible to those skilled in the art, and it is intended in the appended claims to cover all those changes and modifications which fall within the true spirit and scope of the present device.

What is claimed is:

1. An insertion instrument for inserting an artificial disc device having separate upper and lower members in an intervertebral space, the insertion instrument comprising:
    an elongate shaft assembly having proximate and distal ends including a longitudinal axis extending therebetween;
    a gripping mechanism generally at the distal end of the elongate shaft having a holding configuration for securing a portion of the artificial disc device relative the distal end and a releasing configuration to permit removal of the artificial disc device portion from the elongate shaft assembly;
    a handle configured to be held by a user's hand;
    an actuating mechanism between the gripping mechanism and the handle operable to configure the gripping mechanism in the holding configuration and the releasing configuration thereof; and
    a resilient disc holding member of the gripping mechanism;
    an upwardly bowed portion of the resilient disc holding member; and
    a distal holding portion of the upwardly bowed portion configured for securing one of the artificial disc members thereto and extending toward the shaft assembly distal end at a downward incline relative to the longitudinal axis to hold the one artificial disc member secured thereto at a generally corresponding downward incline relative to the longitudinal axis with the resiliency of the resilient disc holding member allowing the upwardly bowed portion to generally flatten out during artificial disc implantation so that the one disc member is oriented to extend generally parallel to the longitudinal axis for implantation in the intervertebral space.

2. The insertion instrument of claim 1, wherein the actuating mechanism includes a trigger configured to be shifted relative to the handle by the hand of the user in a generally neutral wrist position thereof to operate the actuating mechanism.

3. The insertion instrument of claim 2, wherein the actuating mechanism includes a pivot connection between the trigger and the handle so that the trigger is actuated by pivoting the trigger towards the handle.

4. The insertion instrument of claim 2, wherein the actuating mechanism includes a release having a locked configuration interfering with pulling of the trigger toward the handle and an unlocked configuration permitting pulling of the trigger toward the handle.

5. The insertion instrument of claim 1, wherein the handle has a pistol-grip configuration to extend generally transversely from the shaft axis and to depend therefrom so that in use the handle can be grasped substantially free of wrist flexion, extension, ulnar deviation, or radial deviation.

6. The insertion instrument of claim 1, further comprising a locking device that is operable to cooperate with the shaft assembly to substantially restrict movement of the artificial disc relative to the gripping mechanism.

7. The insertion instrument of claim 6, wherein the locking device includes a coupling member extending along the longitudinal axis between the gripping mechanism and the locking device, the coupling member configured to move with the actuating mechanism when the locking device is in an unlocked condition and configured to substantially restrict movement of the actuating mechanism when the locking device is in a locked condition.

8. The insertion instrument of claim 7, wherein the locking device includes a control knob having a selective engagement with the coupling member to permit relative movement therebetween when disengaged and to restrict relative movement therebetween when engaged.

9. The insertion instrument of claim 1, further comprising:
    a lock knob defining a bore therethrough with internal threads on an inner portion of the bore, the lock knob configured to switch between a locked position to restrict movement of the artificial disc relative to the elongate shaft assembly and an unlocked position to permit movement of the artificial disc relative to the elongate shaft assembly;
    a coupling member extending through the bore and having external threads on an outer portion thereof;
    the internal threads of the lock knob mated with the external threads of the coupling member to substantially restrain movement of the artificial disc about the distal end of the elongate shaft in the locked position of the lock knob; and
    the internal threads of the lock knob unmated with the external threads of the coupling member to permit movement of the artificial disc about the distal end of the elongate shaft in the unlocked position of the lock knob.

10. The insertion instrument of claim 9, wherein the lock knob is arranged and configured to turn about the longitudinal axis of the elongate shaft to switch between the mated and unmated configurations of the internal and external threads.

11. The insertion instrument of claim 10, wherein the instrument includes a guide member having a stop thereon positioned to substantially restrict turning of the lock knob to less than about one revolution thereof.

12. The insertion instrument of claim 1, wherein the elongate shaft includes a fixed portion for being coupled to the lower member of the artificial disc device, a lower movable portion configured to slide along the longitudinal axis relative to the fixed portion for being engaged to the lower member of the artificial disc device, and an upper holding portion including the resilient disc holding member configured to pivot relative to the fixed portion for being coupled to the upper member of the artificial disc device to position the upper member of the artificial disc device inclined relative to the lower member.

13. The insertion instrument of claim 12, wherein the upper holding portion of the elongate shaft is pivotally connected to the actuator such that an initial actuation of the actuator permits the holding portion to pivot away from the fixed portion of the elongate shaft to allow the upper member of the artificial disc to be coupled to the distal holding portion thereof.

14. The insertion instrument of claim 1, wherein the resilient biasing member comprises a curved strip configured to resiliently bias the gripping portion via compression of the curved strip, such that one of the separate upper and lower artificial disc device members held by the gripping portion may be shifted between inclined, biased engagement with the other of the artificial disc device members and less inclined or generally uninclined biased engagement with the other of the artificial disc device members while being held with the gripping portion.

15. An insertion instrument for inserting an artificial disc in an intervertebral space, the insertion instrument comprising:
  an elongate shaft assembly having proximate and distal ends including a longitudinal axis extending therebetween;
  a gripping mechanism generally at the distal end of the elongate shaft assembly having an upwardly bowed portion for gripping a portion of the artificial disc, wherein the gripping mechanism has a holding configuration for securing a portion of the artificial disc relative the distal end and a releasing configuration to permit removal of the artificial disc portion from the elongate shaft assembly;
  a handle oriented to extend transversely to the longitudinal axis such that the insertion instrument is held with a substantially neutral wrist position;
  a single actuator comprising a trigger operable to configure the gripping mechanism in the holding configuration upon an initial actuation thereof and the releasing configuration upon a subsequent actuation thereof; and
  a release member connected to the trigger and shiftable between a plurality of positions with respect thereto for allowing selective operation of the trigger, the release member having a locked position, to block operation of the trigger, and an unlocked position, to allow the trigger to be operable to configure the gripping mechanism in the holding and releasing configurations thereof.

16. The insertion instrument of claim 15, further comprising a pivotable upper shaft of the elongate shaft assembly, wherein the release member is configured to be further shiftable to an unlocked loading position, wherein the trigger may be actuated to allow the pivotable upper shaft to pivot away from the elongate shaft assembly to configure the gripping mechanism for coupling at least a portion of the artificial disc device thereto.

17. The insertion instrument of claim 15, wherein the trigger is pivotally connected to the handle and the release member is pivotally connected to the trigger.

18. The insertion instrument of claim 17, wherein the handle comprises a plurality of stop portions that correlate respectively with the plurality of positions of the release member, such that the release member is configured to abut with one of the plurality of stop portions when in one of the correlating plurality of positions thereof to selectively limit the range of motion of the trigger.

19. The insertion instrument of claim 15, wherein the release member is spring biased into the locked position, such that the release member must be positively shifted into the unlocked position to operate the trigger.

20. An insertion instrument for inserting an artificial disc device in an intervertebral space, comprising:
  a handle portion;
  an elongate shaft assembly connected to the handle portion having a longitudinal axis and a distal end opposite the handle portion;
  a gripping mechanism at the distal end of the elongate shaft assembly for securing a portion of the artificial disc device;
  a fixed shaft of the elongate shaft assembly;
  a pivotable upper shaft of the elongate shaft assembly having a distal end and configured to translate along the longitudinal axis with respect to the fixed shaft;
  a first gripping portion of the pivotable upper shaft at the distal end thereof for gripping a portion of the artificial disc device, wherein the first gripping portion of the pivotable upper shaft comprises a yoke grip that is upwardly bowed with respect to the longitudinal axis for holding a portion of the artificial disc device in an inclined orientation with respect to the longitudinal axis when in the insertion configuration; and
  a pivot connection between the pivotable upper shaft and the elongate shaft assembly to allow the pivotable upper shaft to extend adjacent to and along the fixed shaft with the first gripping portion configured to hold at least a portion of the artificial disc device in an insertion configuration, and to be pivotally shifted about the pivot connection away from the fixed shaft to allow at least a portion of the artificial disc device to be connected to the first gripping portion of the pivotable upper shaft in a loading configuration.

21. The insertion instrument of claim 20, wherein the first gripping portion of the pivotable upper shaft comprises a resilient member connected to the upper shaft and is configured to be biased generally towards the longitudinal axis to hold a portion of the artificial disc device in the insertion configuration.

22. The insertion instrument of claim 21, wherein the resilient member comprises a curved strip including the first gripping portion at one end for holding a portion of the artificial disc device.

23. The insertion instrument of claim 22, wherein the first gripping portion of the resilient member comprises a grasping claw including two laterally spaced fingers that form a groove therebetween for securing a post-shaped member of the artificial disc device.

24. The insertion instrument of claim 23, wherein the grasping claw includes alignment portions that extend downwardly toward the fixed shaft and are operable to engage therewith for aligning the claw with respect to the fixed shaft.

25. The insertion instrument of claim 21, wherein the grasping claw of the inclined resilient member is inclined toward the longitudinal axis when the pivotable upper shaft is in the insertion configuration for holding a portion of the artificial disc device in an inclined orientation with respect to the longitudinal axis.

26. The insertion instrument of claim 20, wherein the artificial disc device comprises separate upper and lower members and wherein the elongate shaft assembly comprises a lower shaft configured to translate along the longitudinal axis with respect to the fixed shaft with a second gripping portion at a distal end thereof for gripping the lower artificial disc device member and the upper pivotable shaft is configured to grip the upper artificial disc device member and bias the upper artificial disc device member against the lower artificial disc device member to provide the insertion configuration of the upper and lower artificial disc device members.

* * * * *